United States Patent
Ausserre et al.

(10) Patent No.: US 7,652,762 B2
(45) Date of Patent: Jan. 26, 2010

(54) ANTIGLARE SUPPORTS AND CONTRAST AMPLIFYING SUPPORTS FOR POLARIZED LIGHT REFLECTION

(75) Inventors: Dominique Ausserre, Soulitre (FR); Marie-Pierre Valignat, Princeton, NJ (US)

(73) Assignees: Centre National de la Recherche Scientifique, Paris (FR); Universite Pierre et Marie Curie (Paris 6), Paris (FR)

( * ) Notice: Subject to any disclaimer, the term of this patent is extended or adjusted under 35 U.S.C. 154(b) by 705 days.

(21) Appl. No.: 10/518,075

(22) PCT Filed: Jun. 19, 2003

(86) PCT No.: PCT/FR03/01895

§ 371 (c)(1),
(2), (4) Date: Dec. 2, 2005

(87) PCT Pub. No.: WO04/001399

PCT Pub. Date: Dec. 31, 2003

(65) Prior Publication Data

US 2006/0103933 A1 May 18, 2006

(30) Foreign Application Priority Data

Jun. 19, 2002 (FR) .................................. 02 07599

(51) Int. Cl.
*G01N 21/01* (2006.01)
(52) U.S. Cl. ...................................... 356/244; 356/369
(58) Field of Classification Search ................. 356/369, 356/244, 937; 569/577
See application file for complete search history.

(56) References Cited

U.S. PATENT DOCUMENTS

| | | | |
|---|---|---|---|
| 4,747,674 A * | 5/1988 | Butterfield et al. | 359/590 |
| 5,333,052 A | 7/1994 | Finarov | |
| 5,408,322 A | 4/1995 | Hsu et al. | |
| 5,639,671 A * | 6/1997 | Bogart et al. | 436/518 |
| 5,812,405 A * | 9/1998 | Meredith, Jr. | 700/157 |
| 6,172,812 B1 * | 1/2001 | Haaland et al. | 359/589 |
| 7,130,029 B2 * | 10/2006 | Wack et al. | 356/73 |

(Continued)

FOREIGN PATENT DOCUMENTS

DE  197 08 036  9/1998

(Continued)

OTHER PUBLICATIONS

R.M.A. Azzam and N.M. Bashara, "Ellipsometry and Polarized Light", North-Holland, Elsevier Science Publishers, 1989.*

(Continued)

*Primary Examiner*—Tarifur Chowdhury
*Assistant Examiner*—Michael Lapage
(74) *Attorney, Agent, or Firm*—Young & Thompson

(57) ABSTRACT

A support designed for observing between intersecting polarizers an object located in its vicinity in a medium (3) of index $n_0$ with incident convergent incoherent illumination under an angle $\theta_0$ at a wavelength $\lambda$. The support includes a substrate (1) with complex refractive index $n_2$ and a layer (2) of refractive index $n_1$ and thickness $e_1$. The value of the thickness $e_1$ of the layer (2) is at ±2% such that $d_2V/de^2_1 \ln|\acute{O}|^2 = 0$ with $\acute{O} = \acute{O}_{01} + \acute{O}_{12}(1+\pi_{01})e(-2/\beta_1) + \acute{O}_{01}\pi_{12}e(-4/\beta_1)/1 + r_{01(p)} + r_{12(p)} e(-2/\beta_1)(1 + r_{01(s)}{}^r {}_{12(s)}{}^e(-2/\beta_1))$. Observation devices incorporating such a support are also disclosed.

28 Claims, 4 Drawing Sheets

U.S. PATENT DOCUMENTS 7,307,726 B2 * 12/2007 Ausserre et al. ............. 356/369

FOREIGN PATENT DOCUMENTS

| GB | 2 291 890 | 2/1996 |
|---|---|---|
| GB | 2 352 030 | 1/2001 |

OTHER PUBLICATIONS

Sandstroem et al., "Visual detection of organic monomolecular films by interference colors", Applied Optics, vol. 24, No. 4, Feb. 15, 1985, Optical Society of America.*

Blodgett and Langmuir, "Built-Up Films of Barium Stearate and Their Optical Properties", Physical Review, vol. 51, Jun. 1, 1937, pp. 964-982.*

Dicke J et al:, "Ellipsomicroscopy for surface imaging: contrast mechanism, enhancement, and application to CO oxidatio on Pt(110)" Journal of the Optical Society of America -A, Optical Society of America, Washington, US, vol. 17, No. 1, Jan. 2000, pp. 135-141, XP002182387 ISSN: 1084-7529 p. 137, paragraph 1.

Shatalin S V et al:, "Polarisation contrast imaging of thin films in scanning microscopy", Optics Communications, North-Holland Publishing Co. Amsterdam, NL, vol. 116, No. 4, May 1, 1995, pp. 291-299, XP004011523 ISSN: 0030-4018 p. 292, col. 2, paragraph 3, p. 294, col. 1, paragraph 2.

* cited by examiner

ANTIGLARE SUPPORTS AND CONTRAST AMPLIFYING SUPPORTS FOR POLARIZED LIGHT REFLECTION

FIELD OF THE INVENTION

The present invention concerns object-carrying supports intended for improving the measurements or the reflection observation of thin films or of very small objects under optical microscope or under any other optical imaging instrument: visor, glasses, macroscope, magnifying glass, binocular magnifying glass, camera, photo camera, near-filed microscope, endoscope, cofocal microscope, near field optical microscope (SNOM), biochip readers, magneto-optical reader, confocal microscope. These supports are in particular intended for use in visualisation and measuring techniques in reflection differential interferential contrast (DIC). They are also intended for use in all observation and measuring techniques in polarised light reflection.

These supports are defined either by a set of characteristics which may concern their nature (example: a dielectric layer on a silicon substrate) or their function (example: contrast amplifying support for the observations between crossed polarisers), and which, if they are common to a certain number of these supports, class it in families of supports, or by a set of adjustable parameters which enable to recognise individually the members of a given family.

SUMMARY OF THE INVENTION

The object of the present invention is therefore to offer a support, exhibiting in relation to the thickness $e_1$ and to the index $n_1$ of the layer formed on a substrate of complex refraction index $n_2$, in a surrounding medium of index $n_0$, either a contrast amplifying function for a polarised light observation, or a antiglare function for the polarised light.

To this effect, the invention concerns a support intended for observing between crossed polarisers an object placed on the support or in the vicinity thereof in a medium of index $n_0$ with spatially incoherent incident convergent illumination under an angle $\theta_0$ at a wavelength $\lambda$, including a substrate of complex refraction index $n_2$, a layer of complex refraction index $n_1$ and of thickness $e_1$ The value of the thickness $e_1$ of the layer is within 2% so that:

$$\frac{d^2}{de_1^2}\ln|\sigma|^2 = 0$$

with $$\sigma = \frac{\sigma_{01} + \sigma_{12}(1+\pi_{01})e^{(-2j\beta_1)} + \sigma_{01}\pi_{12}e^{(-4j\beta_1)}}{(1+r_{01(p)}+r_{12(p)}e^{(-2j\beta_1)})(1+r_{01(s)}r_{12(s)}e^{(-2j\beta_1)})}$$

a formula wherein $\sigma_{ij}$ and $\pi_{ij}$ represent respectively the sum and the product of the Fresnel coefficients of the different interfaces [(i,j)=(0,1) or (1,2)]:

$$r_{ij(p)} = \frac{n_j\cos\theta_i - n_i\cos\theta_j}{n_j\cos\theta_i + n_i\cos\theta_j}$$

and $$r_{ij(s)} = \frac{n_i\cos\theta_i - n_j\cos\theta_j}{n_i\cos\theta_i + n_j\cos\theta_j}$$

and wherein $\beta_1 = \frac{2\pi n_1 e_1 \cos\theta_1}{\lambda}$, with $\cos\theta_1 = \sqrt{1-\left(\frac{n_0}{n_1}\right)^2\sin^2\theta_0}$.

The invention also concerns a support intended for observing between crossed polarisers an object placed on the support or in the vicinity thereof in a medium of index $n_0$ with incident convergent incoherent illumination under an angle $\theta_0$ at a wavelength $\lambda$, including a substrate of complex refraction index $n_2$, a layer of complex refraction index $n_1$ and of thickness $e_1$.

The value of the thickness $e_1$ of the layer is within 2% so that:

$$\frac{d}{de_1}|\sigma^2| = 0$$

with $$\sigma = \frac{\sigma_{01} + \sigma_{12}(1+\pi_{01})e^{(-2j\beta_1)} + \sigma_{01}\pi_{12}e^{(-4j\beta_1)}}{(1+r_{01(p)}+r_{12(p)}e^{(-2j\beta_1)})(1+r_{01(s)}r_{12(s)}e^{(-2j\beta_1)})}$$

a formula wherein $\sigma_{ij}$ and $\pi_{ij}$ represent respectively the sum and the product of the Fresnel coefficients of the different interfaces [(i,j)=(0,1) or (1,2)]:

$$r_{ij(p)} = \frac{n_j\cos\theta_i - n_i\cos\theta_j}{n_j\cos\theta_i + n_i\cos\theta_j}$$

and $r_{ij(s)} = \frac{n_i\cos\theta_i - n_j\cos\theta_j}{n_i\cos\theta_i + n_j\cos\theta_j}$ and wherein $\beta_1 = \frac{2\pi n_1 e_1 \cos\theta_1}{\lambda}$, with $\cos\theta_1 = \sqrt{1-\left(\frac{n_0}{n_1}\right)^2\sin^2\theta_0}$.

The invention also concerns a support intended for optimising the useful extinction coefficient of a polarising microscope for observing an object placed on the support or above the support in a medium of index $n_0$ with incident convergent incoherent illumination under an angle $\sigma_0$ at a wavelength $\lambda$, including a substrate of complex refraction index $n_2$, a layer of complex refraction index $n_1$ and of thickness $e_1$.

The value of the thickness $e_1$ of the layer is within 2% so that:

$$\frac{d}{de_1}\left(\frac{|\sigma|^2}{R_{NP}}\right) = 0$$

with $$R_{NP} = \frac{1}{4}|r_p + r_s|^2 + \frac{1}{4}|r_p - r_s|^2$$

and $$r_p = \frac{r_{01(p)} + r_{12(p)}e^{(-2j\beta_1)}}{1+r_{01(p)}r_{12(p)}e^{(-2j\beta_1)}} \text{ and } r_s = \frac{r_{01(s)} + r_{12(s)}e^{(-2j\beta_1)}}{1+r_{01(s)}r_{12(s)}e^{(-2j\beta_1)}}$$

-continued and $$\sigma = r_p + r_s = \frac{\sigma_{01} + \sigma_{12}(1 + \pi_{01})e^{(-2j\beta_1)} + \sigma_{01}\pi_{12}e^{(-4j\beta_1)}}{(1 + r_{01(p)}r_{12(p)}e^{(-2j\beta_1)})(1 + r_{01(s)}r_{12(s)}e^{(-2j\beta_1)})}$$

a formula wherein $\sigma_{ij}$ and $\pi_{ij}$ represent respectively the sum and the product of the Fresnel coefficients of the different interfaces [(i,j)=(0,1) or (1,2)]:

$$r_{ij(p)} = \frac{n_j\cos\theta_i - n_i\cos\theta_j}{n_j\cos\theta_i + n_i\cos\theta_j}$$

and $$r_{ij(s)} = \frac{n_i\cos\theta_i - n_j\cos\theta_j}{n_i\cos\theta_i + n_j\cos\theta_j}$$

and wherein $\beta_1 = \frac{2\pi n_1 e_1 \cos\theta_1}{\lambda}$, with $\cos\theta_1 = \sqrt{1 - \left(\frac{n_0}{n_1}\right)^2 \sin^2\theta_0}$.

The present invention also concerns the characteristics which will appear in the following description and which should be considered individually or according to all their technically possible combinations:
- the values of the refraction index $n_1$ and of the thickness $e_1$ of the layer are within 2% such that:

$$\sigma = 0$$

the substrate and the layer are dielectric or little absorbent, the module of the imaginary portion of their complex index being smaller than 0.01, the general conditions being reduced to the conditions:

$$n_1 e_1 \cos\theta_1 = \frac{\lambda}{4} + k\frac{\lambda}{2}$$

and $$n_1^2 = \frac{n_2^2 + \sqrt{n_2^2 \cos^2\theta_0 (n_2^2 - n_0^2 \sin^2\theta_0)}}{n_2^2 + n_0^2 \cos^2\theta_0}$$

with k integer and with an uncertainty of 2% on the values of $n_1$ and $e_1$;
$\theta_0$ is smaller than 5°, the general conditions being reduced to $$\frac{2}{n_1^2} = \frac{1}{n_0^2} + \frac{1}{n_2^2}$$

and $$n_1 e_1 \cos\theta_1 = \frac{\lambda}{4} + k\frac{\lambda}{2}$$

with k integer and with an uncertainty of 2% on the values of $n_1$ and $e_1$;
the support is intended for use with annular incident illumination with an angle of incidence $\theta_0$ which is unique within ±2.5°;

the support is intended for use in incident and convergent axial illumination with an average angle of incidence $\theta_0$ associated with its total angular opening $\Delta\theta_0$ by the relation:

$$\cos\theta_0 = \cos^2\left(\frac{\Delta\theta_0}{2}\right)$$

the illumination is monochromatic or quasi-monochromatic at the wavelength $\lambda$;
the illumination has a continuous wide spectrum or polychromatic with maximum span ±0.3 $\lambda$ around its average wavelength $\lambda$;
the support being intended for use in the air as a surrounding medium, with $\theta_0=30°$ and $\lambda=589.3$ nm, the substrate is made of cadmium with $n_2=1.13-5.01j$, the layer having an index $n_1=1.42$ and $e_1=1084$ Angströms;
the substrate and the layer have the specificities of the following table wherein $n_1$ and $e_1$ are the index and the thickness of the layer, $n_2$ the complex refraction index of the substrate, in the air as a surrounding medium, $\theta_0=5°$ and $\lambda=540$ nm

| Substrate | $n_2$ | $n_1$ | $e_1$(Å) |
|---|---|---|---|
| Gold | 0.40-2.6j | 1.70 | 694 |
| Silver | 0.13-3.44j | 1.59 | 795 |
| Aluminium | 0.92-0.95j | 2.01 | 346 |
| Nickel | 1.76-3.2j | 1.51 | 847 |

$\theta_0$ is an average angle of incidence equal to 20° and the substrate and the layer have the specificities of the following table wherein $n_1$ and $e_1$ are the index and the thickness of the layer, $n_2$ the complex refraction index of the substrate, in the air as a surrounding medium (3) and $\lambda=540$ nm

| Substrate | $n_2$ | $n_1$ | $e_1$(Å) |
|---|---|---|---|
| Gold | 0.40-2.6j | 1.64 | 739 |
| Silver | 0.13-3.44j | 1.55 | 838 |
| Aluminium | 0.92-0.95j | 1.89 | 399 |
| Nickel | 1.76-3.2j | 1.48 | 890 |

$\theta_0$ is equal to 5° and the substrate and the layer have the specificities of the following table wherein $n_1$ and $e_1$ are the index and the thickness of the layer within 2%, $n_2$ the complex refraction index of the substrate, $n_0$ the index of the surrounding medium, $\lambda=589.3$ nm when the layer is made of cadmium and $\lambda=540$ nm in the other cases

| Substrate | $n_2$ | $n_0$ | $n_1$ | $e_1$ |
|---|---|---|---|---|
| Gold | 0.40-2.6j | 1.33 | 2.42 | 490 |
| Gold | 0.40-2.6j | 1.5 | 1.79 | 755 |
| Silver | 0.13-3.44j | 1.33 | 2.28 | 512 |
| Silver | 0.13-3.44j | 1.5 | 2.7 | 412 |
| Aluminium | 0.92-0.95j | 1 | 1.89 | 399 |
| Nickel | 1.76-3.2j | 1.33 | 2.11 | 572 |
| Nickel | 1.76-3.2j | 1.5 | 2.45 | 473 |
| Cadmium | 1.13-5.01j | 1 | 1.49 | 970 |
| Cadmium | 1.13-5.01j | 1.33 | 2.05 | 684 |
| Cadmium | 1.13-5.01j | 1.5 | 2.36 | 582 |

-continued

| Substrate | $n_2$ | $n_0$ | $n_1$ | $e_1$ |
|---|---|---|---|---|
| Tin | 1.48-5.25j | 1 | 1.48 | 899 |
| Tin | 1.48-5.25j | 1.33 | 2.02 | 640 |
| Tin | 1.48-5.25j | 1.5 | 2.33 | 548 |
| Copper | 1.04-2.59j | 1 | 1.62 | 746 |
| Copper | 1.04-2.59j | 1.33 | 2.23 | 423 |
| Copper | 1.04-2.59j | 1.5 | 2.83 | 351 |
| Iron (evaporated) | 1.51-1.63j | 1 | 1.54 | 737 |
|  | 1.51-1.63j | 1.33 | 2.23 | 423 |
|  | 1.51-1.63j | 1.5 | 2.72 | 305 | the parameters defined by the claims 10 to 14 are kept with the exception of the wavelength λ and of the thickness $e_1$ of the layer 2 which are modified proportionally, $e_1/\lambda$ not being modified.

The invention also concerns an accessory intended for observing a preferably liquid sample formed of a Petri dish and of a support intended for receiving said sample, the support being the bottom of this dish.

The invention also concerns the devices having the following characteristics:
- a device for observing a sample including an optical microscope, a support intended for receiving said sample and two crossed polarisers;
- a device for observing a sample including an optical microscope, an accessory intended for receiving said sample and two crossed polarisers;
- a device for observing a sample including an optical microscope, a support intended for receiving said sample, a polariser and a quarter-wave plate;
- a device for observing a sample including an optical microscope, an accessory intended for receiving said sample, a polariser and a quarter-wave plate;
- a device for observing a sample whereof the optical microscope is fitted with a differential interferential contrast device.

BRIEF DESCRIPTION OF THE DRAWINGS

In different possible embodiments, the invention will be described more in detail with reference to the appended drawings wherein.

DETAILED DESCRIPTION OF THE EMBODIMENTS

To describe completely the invention, the support that it concerns is presented, thereafter, in its context while using simultaneously the definitions of the elements involved and the associated devices with respect to which they should be situated.

Figure 1:
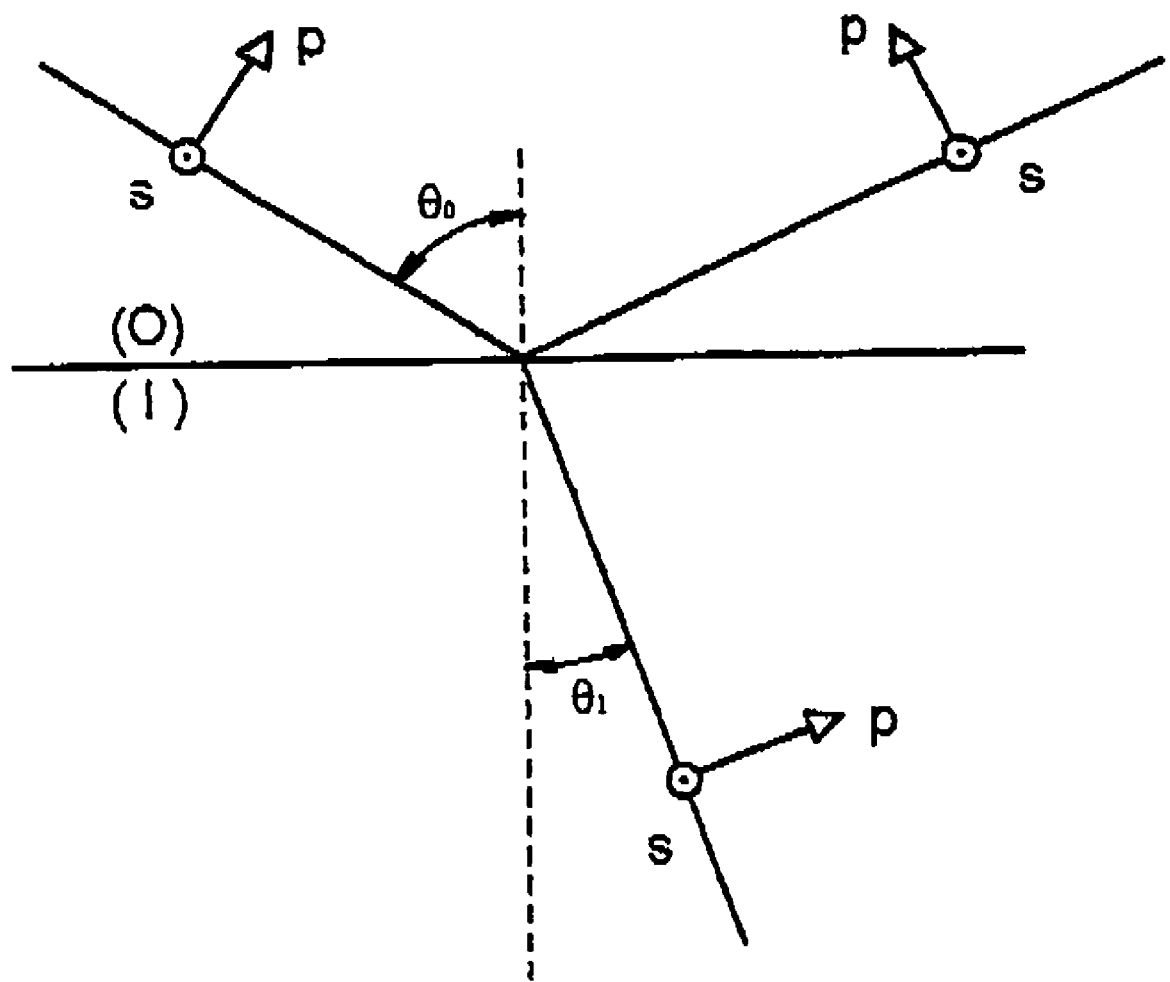
FIG. 1 is a schematic representation of the oblique transmission and reflection of a planar wave at the planar interface between two semi-infinite media 0 and 1.

I. Conventions:

The sign conventions adopted are those represented in FIG. 1 and described also in the book of Azzam and Bashara entitled "ellipsometry and polarised light", North Holland, p 271.

This figure represents the oblique transmission and reflection of a planar wave at the planar interface between two semi-infinite media 0 and 1. $\theta_0$ and $\theta_1$ are respectively the angles of incidence and of refraction. p and s are respectively the polarisations parallel and perpendicular to the plane of incidence. The vector generated $\hat{p} \times \hat{s}$ of the unit vectors along these axes is parallel to the direction of propagation and oriented in the direction of the propagation.

II. Definitions:

By "support" is meant the association of a solid substrate 1 of complex index of refraction $n_2$ and of a coating including at least one layer 2 of thickness $e_1$ and of complex refraction index $n_1$. This support is placed in a surrounding medium 3 of index $n_0$.

By "sample" is meant the association of the object-carrying support and of the object it carries, said support being the object of the invention.

By "observation" is meant a direct ocular observation through an instrument or the acquisition of an image or of a signal by detection means including a recording device such as an analog or digital camera, a COD array or a measuring device such as a detector (photovoltaic cell, photomultiplier) or a matrix of detectors (array of photodiodes, CCD, . . . ) placed in a plane where the image of the sample is formed.

A perfectly reflecting support is defined by the relations $$|r_p| = |r_s| = 1 \tag{E1}$$

on its Fresnel coefficients $r_p$ and $r_s$.

"The standardised intensity" of the image of a support or of a sample obtained by means of an imaging device operating in reflection and including possibly one or several polarising elements and/or modifying the polarisation of the light and collected by means of detection or of observation is defined by the ratio $$R = \frac{I}{I_0} \text{ where } I = I(x, y)$$

designates the intensity collected at one point (x, y) of the image and where $I_0 = I_0(x, y)$ designates the intensity collected at one point (x, y) of the image by the same means of detection or of observation adjusted similarly failing any polariser and while using a perfectly reflecting support.

An "antiglare" (AR) support is defined as having a minimal coefficient of reflection on the set of its adjustable parameters. It relates to the conditions of observation or of measurement. An ideal antiglare support is such that its coefficient of reflection is nil.

A "contrast amplifying" support is defined so that the object that it carries is observed with a contrast made maximal or so that a physical quantity of the object is measured with a sensitivity made maximal on the set of its adjustable parameters. It is also relative to the conditions of observation or of measurement. It is moreover relative to the nature of the object observed. When the nature of the object is not specified, the object will be defined by default as a thin film of thickness 1 Angström (Å) and of index n identical to that of the surface of the support, i.e. of the material forming the layer 2 in contact with the object.

III. Illumination Conditions:

"The convergent axial illumination" is convergent and with radial symmetry around the normal to the surface, defined as "the axis" below in the description, with an opening angle $\theta_0$. The angles of incidence partaking of the illumination cone are therefore all the angles ranging between 0 and $\theta_0$.

<<The annular illumination>> also possesses a radial symmetry around the normal to the surface, i.e. the axis, but it is defined by a single angle of incidence $\theta$ better than within 5 degrees. The "anisotropic" illumination is defined in that a radial symmetry of the azimuths $\phi$ is broken, but the symmetry with respect to the axis kept, and finally "the oblique illumination" is defined by a single angle of incidence $\theta$ and a single azimuth $\phi$.

Except when specified, the illumination will be considered as annular in the remainder of the description. However, the supports described for use under annular illumination with an angle of incidence $\theta_0$ are also intended for use with convergent axial illumination with an average angle of incidence $\theta_0$.

When the illumination is convergent axial, by "average angle" $\theta_0$ is meant the angle defined by the circle separating the illuminating cone in two solid angles of the same value. The support is therefore intended for use under convergent illumination with angular opening $\Delta\theta_0$ and centred on $\theta_0$, where $\theta_0$ is the average angle of incidence ranging 0 and $\Delta\theta_0$ defined by the relation $$\cos\theta_0 = \cos^2\left(\frac{\Delta\theta_0}{2}\right)$$

(FIG. 2).

By default, the collection of the light by the means of detection or of observation is supposed with radial symmetry around the normal to the surface, with the same unique angle of collection or the same opening angle as the illumination, in the remainder of the description.

The illumination is spatially incoherent, which means that a light beam partaking of the illumination may only interfere with itself. Under these conditions, the contributions to the formation of the image must be added in amplitude along a beam and in intensity on the set of beams, i.e. on the set of angles of incidence $\theta$ and of the azimuths $\phi$ contributing to the illumination.

The Fresnel coefficients $r_p$ and $r_s$ are complex functions of $\theta$. In the case of anisotropic supports, these are moreover functions of $\phi$. But the support is supposedly isotropic in the remainder of the description excepted when specified.

Similarly, the illumination is supposedly monochromatic or quasi-monochromatic, the light beam being centred on a wavelength $\lambda$. However, the supports described for use under quasi-monochromatic illumination at the wavelength $\lambda$ are also intended for use with a white light or polychromatic illumination, the spectrum of the illumination being then centred on $\lambda$.

IV. Conditions of Polarisation

IV.1) Non-Polarised Light:

The standardised intensity $R_{NP}$ is written:

$$R_{NP} = \frac{1}{2}(|r_p|^2 + |r_s|^2) \quad (E2)$$

It is equal to 1 for a perfectly reflecting support.

The reflection coefficient of the support is defined by this standardised intensity in non-polarised light. It depends on the illumination conditions.

Figure 2:
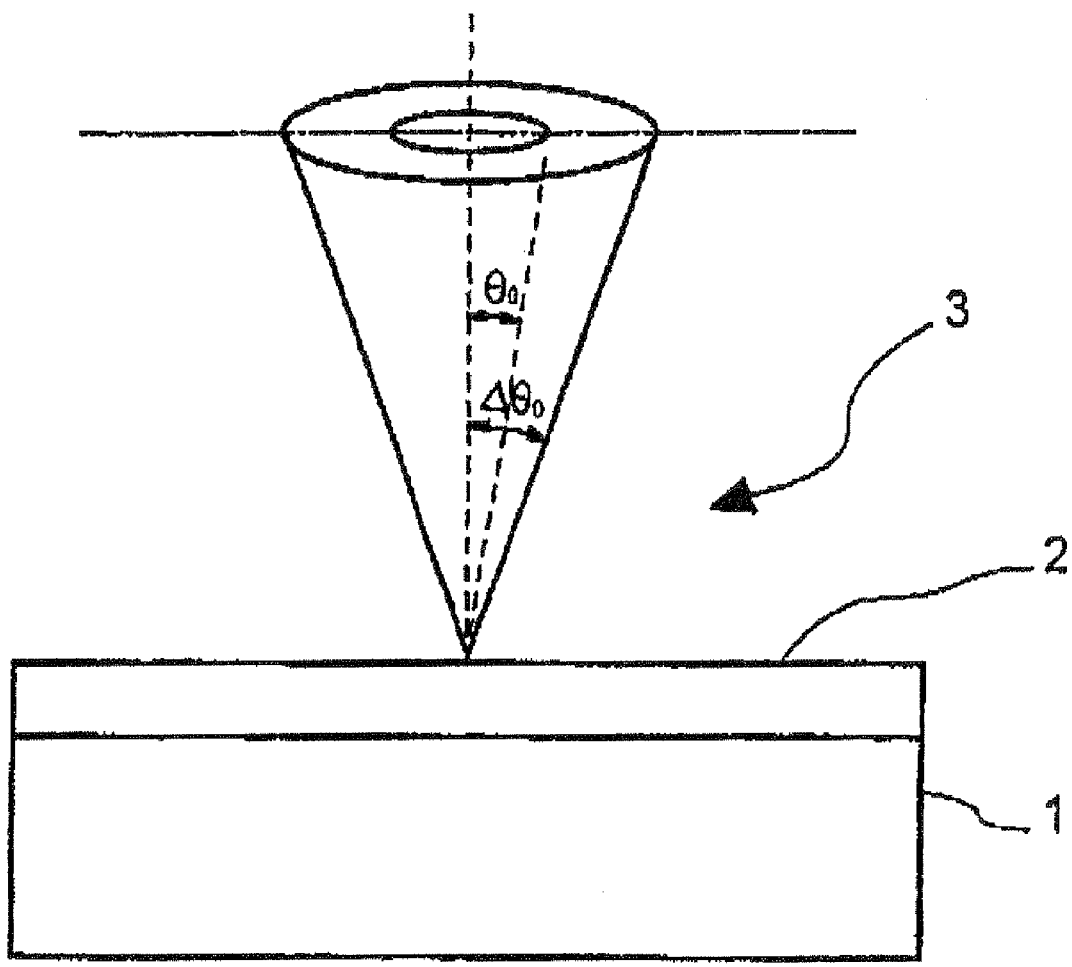
FIG. 2 is a schematic representation of a support, according to the invention.
Figure 2A:
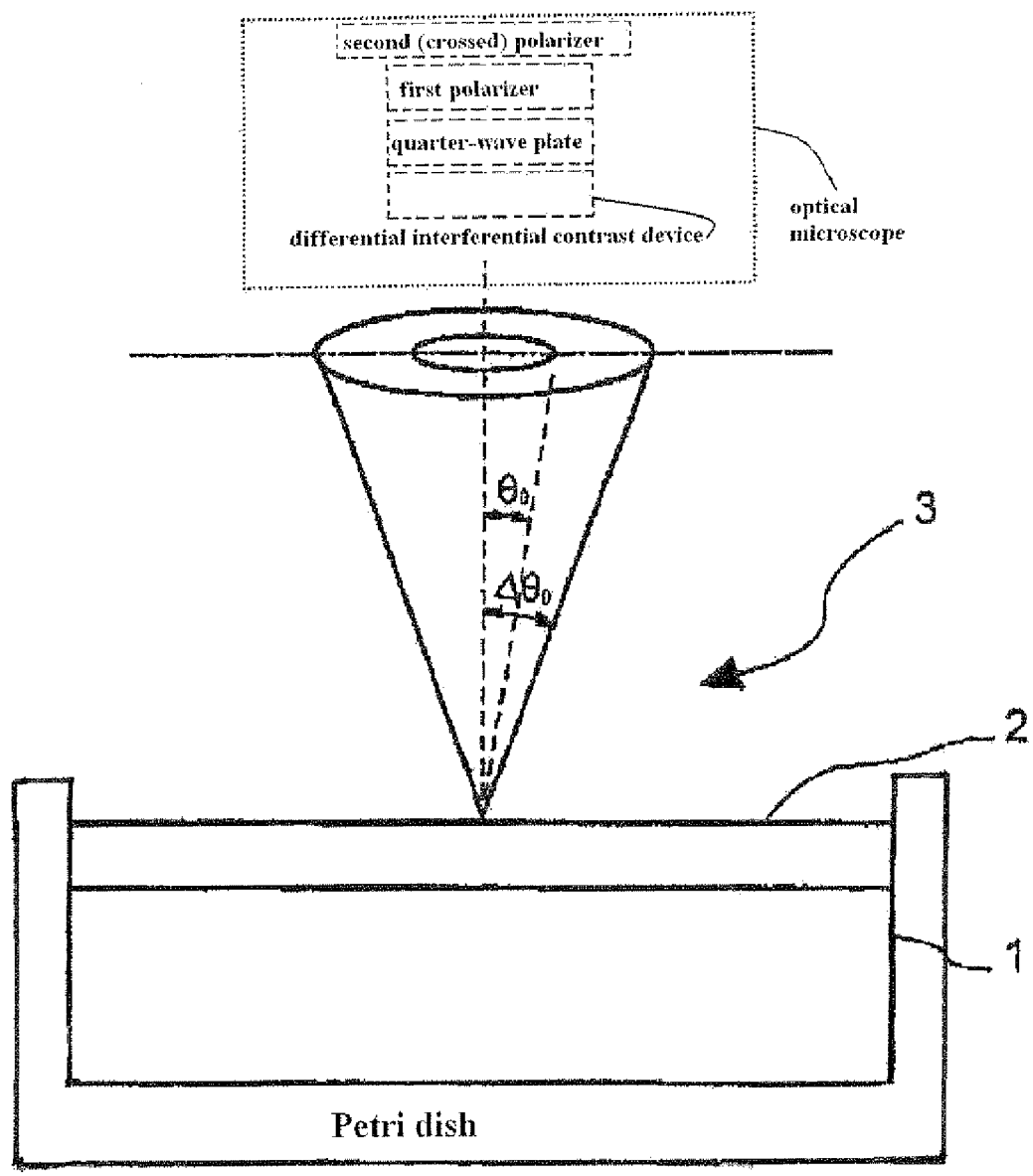
FIGS. 2A and 2B are schematic representations of embodiments of the invention.
Figure 2B:
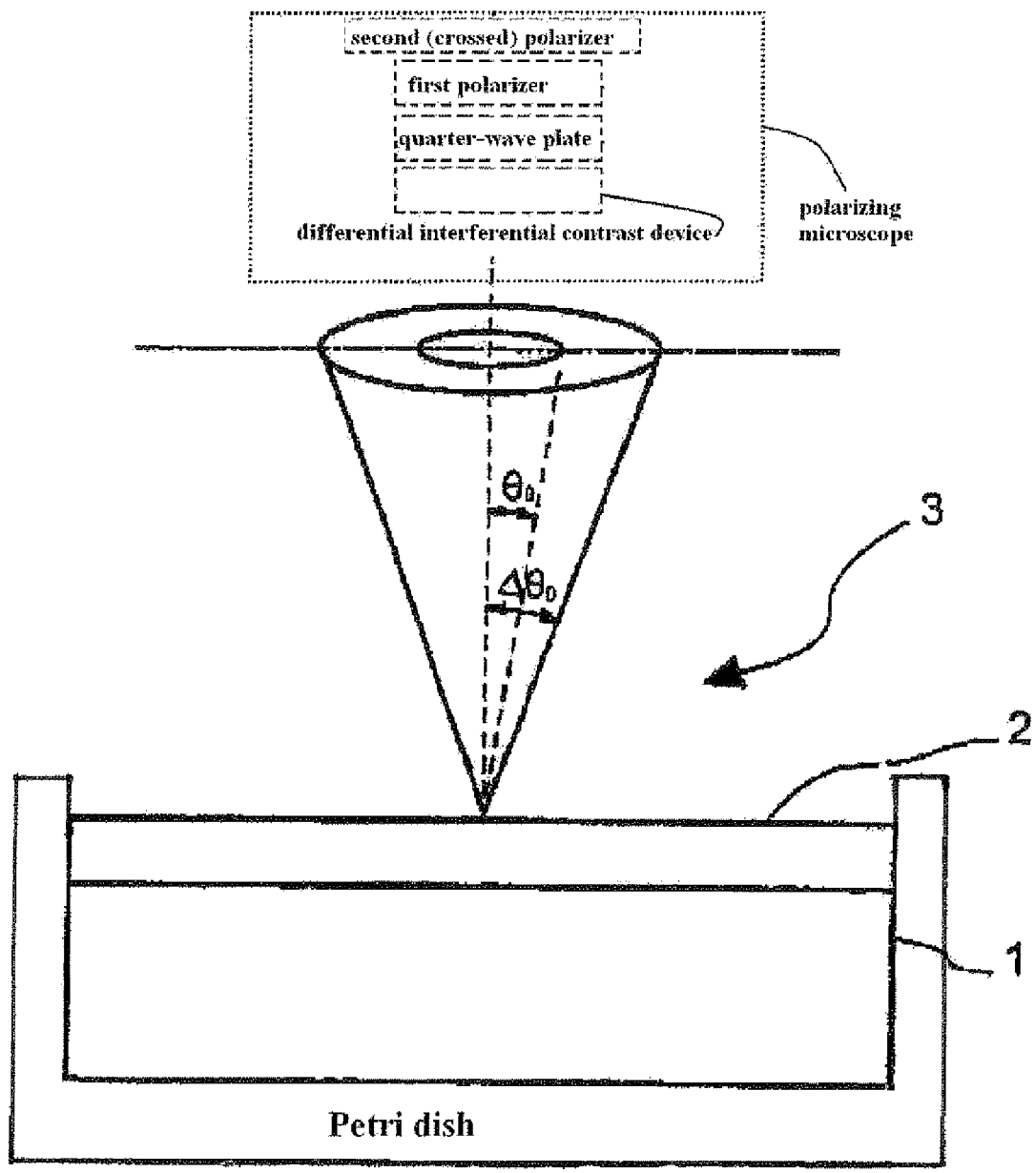

With respect to FIGS. 2A and 2B, the invention also concerns an accessory intended for observing a preferably liquid sample formed of a Petri dish and of a support intended for receiving said sample, the support being the bottom of this dish.

The invention also concerns the devices having the following characteristics:
- a device for observing a sample including an optical microscope, a support intended for receiving said sample and two crossed polarisers;
- a device for observing a sample including an optical microscope, an accessory intended for receiving said sample and two crossed polarisers;
- a device for observing a sample including an optical microscope, a support intended for receiving said sample, a polarizer and a quarter-wave plate;
- a device for observing a sample including an optical microscope, an accessory intended for receiving said sample, a polarizer and a quarterwave plate;
- a device for observing a sample whereof the optical microscope is fitted with a differential interferential contrast device.

IV.2) Polarised Light:

The sample is placed between a first and a second polarisers. In a preferred embodiment and for the remainder of the description, said polarisers will be considered as linear. When said sample is illuminated by a light beam, the beam traverses on its optical path the first polariser which defines its polarisation, then after interaction with the sample, the light beam traverses the second polariser. The first polariser is called "illumination polariser". The second polariser is the analysis polariser or "analyser". The first and the second polarisers form together an angle $\phi$ modulo $\pi$.

The standardised intensity $R(\phi)$ is written:

$$4R(\phi) = \cos^2\phi(|r_p|^2 + |r_s|^2) - \frac{\cos2\phi}{4}|r_p + r_s|^2 \quad (E3)$$

or, similarly:

$$4R(\phi) = \frac{1}{2}(|r_p|^2 + |r_s|^2) + \frac{\cos2\phi}{4}|r_p - r_s|^2 \quad (E4)$$
$$= R_{NP} + \frac{\cos2\phi}{4}|r_p - r_s|^2$$

In the particular case where the first and second polarisers are parallel, it reads:

$$4R(0) = (|r_p|^2 + |r_s|^2) - \frac{1}{4}|r_p + r_s|^2 \quad (E5)$$
$$= 2R_{NP} - \frac{1}{4}|r_p + r_s|^2$$

or, similarly:

$$4R(0) = \frac{1}{2}(|r_p|^2 + |r_s|^2) + \frac{1}{4}|r_p - r_s|^2 \quad \text{(E6)}$$
$$= R_{NP} + \frac{1}{4}|r_p - r_s|^2$$

In the particular case where the first and second polarisers are perpendicular, i.e. crossed, it reads:

$$4R\left(\frac{\pi}{2}\right) = \frac{1}{4}|r_p + r_s|^2 \quad \text{(E7)}$$

or, similarly:

$$4R\left(\frac{\pi}{2}\right) = \frac{1}{2}(|r_p|^2 + |r_s|^2) - \frac{1}{4}|r_p - r_s|^2 \quad \text{(E8)}$$
$$= R_{NP} - \frac{1}{4}|r_p - r_s|^2$$

In the particular case where both polarisers form together an angle $\pi/4$, it reads:

$$4R\left(\frac{\pi}{4}\right) = \frac{1}{2}(|r_p|^2 + |r_s|^2) \quad \text{(E9)}$$
$$= R_{NP}$$

Thus, the standardised intensity may be modulated around its average value $R_{NP}/4$ with an amplitude $$\frac{1}{16}|r_p - r_s|^2$$

by relative rotation of the analyser and of the illumination polariser.

If one considers $$R^+ \equiv \frac{1}{4}|r_p + r_s|^2 \quad \text{and} \quad R^- \equiv \frac{1}{4}|r_p - r_s|^2.$$

Then:

$$4R(\phi) = 2R_{NP}\cos 2\phi - R^+\cos 2\phi \quad \text{(E3-E4 bis)}$$
$$= R_{NP} + R^-\cos 2\phi$$
$$= R^+ + 2R^-\cos 2\phi$$

$$4R(0) = 2R_{NP} - R^+ \quad \text{(E5-E6 bis)}$$
$$= R_{NP} + R^-$$

$$4R\left(\frac{\pi}{2}\right) = R^+ \quad \text{(E7-E8 bis)}$$
$$= R_{NP} - R^-$$

The support of the invention is intended for use between a first and a second crossed polarisers. The light beam incident on the support is therefore polarised.

V. Antiglare Supports and Coatings

V.1) Non-Polarised Light.

It is known that in non-polarised light, an antiglare support (AR) placed in a surrounding medium of index $n_0$ exhibits a coefficient $R_{NP}$ which is minimum. The ideal antiglare support, which verifies $R_{NP}=0$ may only be obtained for a single angle of incidence $\theta_0=0$ and may only be realised on a substrate 1 of index $n_2$ different of $n_0$ where $n_2$ is the complex refraction index of the substrate 1, only by applying a single layer 2 of optical thickness $\lambda/4$ and of optical index $n_1$ so that:

$$n_1 = \sqrt{n_0 n_2} \quad \text{(E10)}$$

$n_0$ being the optical index of the incident medium.

The optical thickness $\lambda/4$ means that the physical thickness $e_1$ of the layer 2 is linked with the wavelength $\lambda$ of the light beam enabling the illumination and with the direction $\theta_1$ of said beam with respect to the normal to the surface after refraction in the layer 2, or refracted angle of incidence, by the relation:

$$n_1 e_1 \cos\theta_1 = \frac{\lambda}{4} + k\frac{\lambda}{2} \quad \text{(E11)}$$

with k integer and $$\cos\theta_1 = \sqrt{1 - \left(\frac{n_0}{n_1}\right)^2 \sin^2\theta_0}.$$

In the case considered, this relation is therefore reduced to:

$$n_1 e_1 = \frac{\lambda}{4} + k\frac{\lambda}{2} \quad \text{(E11 bis)}$$

Let us remind that the refracted angle $\theta_1$ is linked with the incident angle $\theta_0$ on the support by the Snell relation: $n_1 \sin\theta_1 = n_0 \sin\theta_0$ where $n_0$ is the optical index of the incident medium. Similarly, we have $n_2 \sin\theta_2 = n_0 \sin\theta_0$. Let us remind that $\sin^2\theta_i + \cos^2\theta_i = 1$ in all the media.

In practice, it is often preferable to use supports AR which are ideal but little sensitive to the wavelength $\lambda$ or to the angle of incidence $\theta_0$ of the incident light beam. These supports are obtained by multilayer stacks called anti-reflection treatments. In an embodiment, these treatments are used for eliminating the reflections on spectacle glasses or for eliminating the spurious light generated by the reflections on the dioptres of the optical systems.

There exist however other cases where the supports AR, more selective and more efficient, are sought after, for example, for preparing transmission narrow pass-band interferential filters.

V.2) Polarised Light Supports and Coatings "AR-Pol"

The invention concerns supports similar to the antiglare supports, but intended for use in polarised light. They differ from antiglare supports by their composition and by their optical properties. We shall designate it as "AR-Pol".

These new supports form a set which even wider and more diversified than the conventional antiglare supports, and may intervene as accessories or as components in numerous methods or devices. This set is the first object of the present invention. It is subdivided in families corresponding to groups by nature or by function whereof we shall give here a few examples. Each family is designated as "AR-( )-Pol-( )-( ) . . . ", where the successive brackets represent the additional precisions enabling to define it.

From equations E2 to E9 can be derived the following order relations:

$$R\left(\frac{\pi}{2}\right) \leq R(\phi) \tag{I1}$$

For any $\phi$, and:

$$4R\left(\frac{\pi}{2}\right) \leq 4R\left(\frac{\pi}{4}\right) = R_{NP} \leq 4R(0) \tag{I2}$$

As shown by the inequalities I1 and I2, the standardised intensity of the image of a support or of an isotropic sample is always smaller between two crossed polarisers than for any other relative orientation of the polarisers and in the absence of polariser.

V.3) Polarising Microscope:

As it is known, the extinction coefficient $C_e$ of a polarising microscope, is one of its important technical characteristics. It must also be as small as possible. In the case of a reflection-operating microscope, it is defined as the ratio of the intensities reflected by a perfectly reflecting support placed on the one hand between a first and a second crossed polarisers and on the other hand, between a first and a second parallel polarisers, i.e.:

$$Ce = \frac{I_0\left(\frac{\pi}{2}\right)}{I_0(0)} \tag{E14}$$

The examination of the equations E5 and E7 shows that the definition of the perfectly reflecting support given by the equations E1 is not sufficient since the intensity collected $I(\phi)$ depends on the relative phases of both Fresnel coefficients $r_p$ and $r_s$ through their sum. As the purpose of the extinction coefficient is to characterise the microscope properly speaking, it is necessary to introduce more precision in the definition of the perfectly reflecting support while considering either the virtual condition $r_p = r_s = 1$, or the condition $r_p = -r_s = 1$. The first condition not being physically realistic, it is therefore eliminated to keep only the second. Moreover, one always has $r_p = -r_s$ for an angle of incidence of the light beam on the support so that $\theta_0 = 0$, which enables to associate the coefficient Ce=0 to the ideal microscope. We define the Useful extinction coefficient of the set formed by the microscope and the sample as the ratio:

$$C_u = \frac{I\left(\frac{\pi}{2}\right)}{I(0)} \tag{E15}$$

the sample being at least formed of a support.

For a reflection-operating polarising microscope, the value of $C_u$ is derived directly from the equations E6 and E8:

$$C_u = \frac{R_{NP} - \frac{1}{4}|r_p - r_s|^2}{R_{NP} + \frac{1}{4}|r_p - r_s|^2} \tag{E16}$$

$$= \frac{R_{NP} - R^-}{R_{NP} + R^-}$$

Which also reads:

$$C_u = \frac{\frac{1}{4}|r_p + r_s|^2}{2R_{NP} - \frac{1}{4}|r_p + r_s|^2} \tag{E16 bis}$$

$$= \frac{R^+}{R_{NP} - R^+},$$

since:

$$R_{NP} = \frac{1}{4}|r_p + r_s|^2 + \frac{1}{4}|r_p - r_s|^2 \tag{E16 ter}$$

$$= R^+ + R^-$$

Maximisation of the Extinction Coefficient:

The ideal antiglare support corresponds to $R_{NP} = 0$. According to the equation E2, this implies simultaneously $r_p = 0$ and $r_s = 0$, and therefore $R(\phi) = 0$ regardless of the value of $\phi$. The useful extinction coefficient is not defined any longer. One may then, by extension, define it as:

$$C_u = \lim_{R_{NP} \to 0} Cu, \tag{E17}$$

which enables to include the limit case of the ideal antiglare support in the following discussion.

According to the equation E16 bis, the useful extinction coefficient $C_u$ is an increasing function of the ratio $$\frac{|r_p + r_s|^2}{R_{NP}}.$$

To improve the extinction coefficient, and therefore to reduce it, it is this ratio which should be minimised.

VI. Antiglare Supports Between Crossed Polarisers AR-X-Pol

We shall define the family of the supports AR-X-Pol as the family of the supports for which the ratio $$\frac{|r_p + r_s|^2}{R_{NP}}$$

is made minimal, which represents a rule for designing said support. Similarly, we shall give the following functional definition: it is the family of the supports which optimise the useful extinction coefficient of the set [microscope+support] for an ideal polarising microscope.

The ideal supports AR-X-Pol are obtained when this minimum value is nil. They are therefore given by the condition $\sigma=0$.

We shall define the coating AR-X-Pol as the layer 2 which enables to transform a given substrate 1 in a support AR-X-Pol.

VI.1) Supports AR-X-Pol-SD-1D

These supports correspond to the case where the materials used for the substrate 1 and the layer 2 are non absorbent, which means that the modulus of the imaginary portion of their index is smaller than 0.01.

The expression of $r_p$ and $r_s$ for a solid of optical index $n_2$ covered with a single layer 2 of index $n_1$ and of thickness $e_1$ in a surrounding medium of index $n_0$ is conventionally given by:

$$r_m = \frac{r_{01(m)} + r_{12(m)}e^{(-2j\beta_1)}}{1 + r_{01(m)}r_{12(m)}e^{(-2j\beta_1)}} \quad (E17)$$

[Azzam and Bashara, "ellipsometry and polarised light", North-Holland, 1987], with: either m=s, or m=p, according to the polarisation considered and with:

$$\beta_1 = \frac{2\pi n_1 e_1 \cos\theta_1}{\lambda} \quad (E18)$$

where $\cos\theta_1 = \sqrt{1 - \left(\frac{n_0}{n_1}\right)^2 \sin^2\theta_0}$.

This equation enables to read:

$$\sigma = r_p + r_s \quad (E19)$$

$$= \frac{\sigma_{01} + \sigma_{12}(1+\pi_{01})e^{(-2j\beta_1)} + \sigma_{01}\pi_{12}e^{(-4j\beta_1)}}{(1 + r_{01(p)}r_{12(p)}e^{(-2j\beta_1)})(1 + r_{01(s)}r_{12(s)}e^{(-2j\beta_1)})}$$

where $\sigma_{ij}$ and $\pi_{ij}$ represent respectively the sum and the product of the Fresnel coefficients:

$$r_{ij(p)} = \frac{n_j\cos\theta_i - n_i\cos\theta_j}{n_j\cos\theta_i + n_i\cos\theta_j} \quad (E20)$$

and $$r_{ij(s)} = \frac{n_i\cos\theta_i - n_j\cos\theta_j}{n_i\cos\theta_i + n_j\cos\theta_j} \quad (E21)$$

VI.1-1) Ideal Supports AR-X-Pol-SD-1D

These supports are obtained when $\sigma=0$ (E19 bis)

Contrary to the condition [$R_{NP}=0$] which defines the ideal conventional antiglare supports, the condition $\sigma=0$ is always verified in normal incidence. The cases wherein this condition is also verified for a non-zero angle of incidence will be examined below.

The materials considered being dielectric or quasi-dielectric, $r_{ij(p)}$ and $r_{ij(s)}$ are real, and therefore $\sigma_{ij}$ and $\pi_{ij}$ are real.

The situation sought after corresponds therefore to the case where $e^{-2j\beta_1}$ is real, which implies, either:

$$2\beta_1 = (2k+1)\pi \quad (E22)$$

or:

$$2\beta_1 = 2k\pi \quad (E23)$$

with k integer, i.e. either:

$$n_1 e_1 \cos\theta_1 = \frac{\lambda}{4} + k\frac{\lambda}{2} \quad (E24)$$

or:

$$n_1 e_1 \cos\theta_1 = k\frac{\lambda}{2} \quad (E25)$$

The condition E24 is identical to the condition E11 which is one of the relations defining the conventional antiglare supports. One has therefore $e^{-2j\beta_1}=\pm 1$. Looking for solutions of the equation (E19 bis) is reduced to solving the equations:

$$\sigma_{01}(1+\pi_{i2}) - \sigma_{12}(1+\pi_{01}) = 0 \quad (E26)$$

and:

$$\sigma_{01}(1+\pi_{12}) + \sigma_{12}(1+\pi_{01}) = 0 \quad (E27)$$

It should be noted $c_k^2 = \cos^2\theta_k$ and $s_k^2 = \sin^2\theta_k$ for all the media.

Recall the Snell relation: $n_k \sin\theta_k = n_0 \sin\theta_0$

It is easy to establish:

$$\sigma_{ij} = \frac{2n_i n_j(c_i^2 - c_j^2)}{n_i n_j(c_i^2 + c_j^2) + c_i c_j(n_i^2 + n_j^2)} \quad (E28)$$

and:

$$1 + \pi_{ij} = \frac{2n_i n_j(c_i^2 + c_j^2)}{n_i n_j(c_i^2 + c_j^2) + c_i c_j(n_i^2 + n_j^2)} \quad (E29)$$

hence:

$$\frac{\sigma_{ij}}{1+\pi_{ij}} = \frac{(c_i^2 - c_j^2)}{(c_i^2 + c_j^2)} \quad (E30)$$

The equation E26 is thus reduced to:

$$c_0 c_2 = c_1^2 \quad (E31)$$

which reads then:

$$2n_0^2 n_2^2 - n_1^2(n_0^2 + n_2^2) = (n_0^2 n_2^2 - n_1^4)\sin^2\theta_1 \quad (E32)$$

This equation may be solved without any difficulty with respect to each of its parameters.

It is never satisfied with a conventional antiglare support.

In the case where the angle of incidence is very small, this condition is reduced to:

$$\frac{2}{n_1^2} = \frac{1}{n_0^2} + \frac{1}{n_2^2} \quad (E33)$$

The couple of equations E25 and E27 has no solution for $n_0 \neq n_2$.

Both formulas E24 and E32 (or similarly E35 bis) define the family of ideal supports AR-X-Pol-SD-1D for a random angle of incidence defined indifferently by its value $\theta_0$ in the surrounding medium (3) or by its refracted value $\theta_1$ in the layer (2) and also for a convergent axial illumination defined by an average refracted angle $<\theta_1>$.

Both formulas E24 and E33 define the sub-family of ideal supports AR-X-Pol-SD-1D for an optical instrument with an annular illumination defined by a refracted angle of incidence $\theta_1$ or with a convergent axial illumination with small opening and defined by an average refracted angle $<\theta_1>$.

Properties of the Equations E32 and E33 and Consequences:

The 4 variables $n_0$, $n_2$, $n_1$ and $$\sin\theta_1 = \frac{n_0}{n_1}$$

sin $\theta_0$ are not independent. It suffices to consider the reduced variables $$x = \left(\frac{n_1}{n_0}\right)^2 \text{ and } y = \left(\frac{n_2}{n_0}\right)^2$$

to describe all the situations.

The equation E32 then becomes:

$$x^2(y+c_0^2)-2xy+ys_0^2=0 \qquad (E34)$$

whereof the solutions are given by
i) the solutions in x:

$$x = \frac{y + c_0\sqrt{y(y - s_0^2)}}{y + c_0^2} \qquad (E35)$$

which can also read:

$$n_1^2 = \frac{n_2^2 + \sqrt{n_2^2\cos^2\theta_0(n_2^2 - n_0^2\sin^2\theta_0)}}{n_2^2 + n_0^2\cos^2\theta_0} \qquad (E35bis)$$

ii) the solutions in y:

$$y = \frac{c_0^2 x^2}{c_0^2 - (x - 1)^2} \qquad (E36)$$

iii) the solutions in $\theta_0$:

$$c_0^2 = \frac{y(x-1)^2}{y-x^2} = \frac{n_2^2(n_1^2 - n_0^2)^2}{n_0^2(n_0^2 n_2^2 - n_1^4)} \qquad (E37)$$

iv) the variation of x with the angle of incidence $\theta_0$:

$$\frac{dx}{d\theta_0} = -\sin2\theta_0 \frac{2y(x-1)(y-x)}{(y-x^2)^2} = -\sin2\theta_0 \frac{2n_0^2 n_2^2(n_1^2 - n_0^2)(n_2^2 - n_0^2)}{(n_0^2 n_2^2 - n_1^4)^2} \qquad (E38)$$

which shows that the optimal index $n_1$ of the layer 2 decreases when the angle of incidence increases.

For small incidences, the evolution of $n_1$ with $\theta_0$ is described by the approximation:

$$x \approx \frac{2y}{(1+y)}\left(1 - \frac{(y-1)^2}{4y(y+1)}\theta_0^2\right) = \frac{2n_2^2}{(n_0^2 + n_2^2)} \qquad (E39)$$

i.e.:

$$n_1^2 \approx \frac{2n_0^2 n_2^2}{(n_0^2 + n_2^2)} - n_0^2\left(\frac{n_2^2 - n_0^2}{n_2^2 + n_0^2}\right)^2 \frac{\theta_0^2}{2} \qquad (E40)$$

which shows again that the optimal index decreases when the angle of incidence increases.

This dependence is the smaller as y is close to 1.

Still, for a perfect microscope ($C_e$=0), the useful extinction coefficient is always nil in normal incidence ($C_u$=0).

An optimised support AR-X-POL for a non-zero angle, for example of the order of 20 degrees, is optimal for working with a corresponding annular illumination. But moreover, since it enables to obtain $C_u$=0 simultaneously for a zero incidence and for a non-zero incidence, it enables to keep an excellent useful extinction coefficient on the set of the opening cone of a convergent axial illumination, from 0 to 30 degrees for instance. This constitutes a considerable advantage of the coatings AR-X-POL on the conventional antiglare coatings for all the applications of the antiglare supports compatible with the use of a polarised light.

This flexibility on the angle of incidence translates by an analogue flexibility on the wavelength of the small incidence illumination. Indeed, by logarithmic differentiation of the equation E24 for instance, we obtain:

$$-\tan(\theta_1)\Delta\theta_1 = \frac{\Delta\lambda}{\lambda}$$

which shows that a variation in wavelength as high as 30% with an annular illumination is equivalent to an opening of 30 degrees on a convergent illumination with a fixed wavelength. This variation in wavelength covers the whole visible spectrum around $\lambda$=0.55 μm.

If, on the contrary, it is desirable to exploit the colouring effects for detection purposes, the use of an annular illumination with high angle of incidence enables to bring high sensitivity to the wavelength.

The supports and coatings AR-X-Pol are therefore particularly advantageous for uses in white light.

The index $n_1$ of the layer 2 is intermediate between the index $n_2$ of the substrate 1 whereon it is formed and the index $n_0$ of the surrounding medium. The equations E32 and E33 are symmetrical in $n_0$ and $n_2$.

This shows that said layer 2 possesses the same properties as the light reflecting from the small index medium to the high index medium or from the high index medium to the small index medium.

Thus, one may extinguish the reflection of a polarised light when the substrate 1 is the end of an optical fibre, or a waveplate or the bottom of a Petri dish when observed from beneath on a reversed microscope.

VI.1 -2) Approximate Supports AR-Pol-X-SD-1D

When the three indices ($n_0$, $n_1$ and $n_2$) are imposed or constrained, the minimum of |σ| with respect to $e_1$ is not nil if the condition E32 is not verified, but this minimum exists nevertheless and corresponds to the best possible extinction taking the constraints into account.

The best possible extinction between crossed polarisers is thus obtained by seeking the minimum of $|\sigma|$ (or similarly that of $|\sigma|^2$) with respect to $e_1$. With $\theta_1$ and $n_1$ fixed, this amounts to looking for it with respect to $\beta_1$. Let us assume $z=e^{-2j\beta_1}=\cos 2\beta_1 - j \sin 2\beta_1$. The expression of $\sigma$ given by the equation E19 is the ratio of 2 polynomials of degree 2 in z. Since $|z|=1$, the square of the modulus of each of these polynomials only contains constant terms, $\cos 2\beta_1$ terms and $\cos 4\beta_1$ terms. The derivate of their ratio is therefore proportional to $\sin 2\beta_1$. The solutions of $\sin 2\beta_1 = 0$ are therefore solutions of the equation $$\frac{d|\sigma|^2}{d\beta_1} = 0.$$

One finds therefore the solutions given by the equations E24 and E25. Thus, even when the conditions E32 or E33 are not satisfied, one may optimise the thickness of the layer 2 to optimise the useful extinction coefficient under a polarising microscope, and this optimum value corresponds either to a layer 2" at $\lambda/4$", or to a layer 2" at $\lambda/2$".

VI.2) Supports AR-X-Pol-1

We shall describe here the rules for building supports AR-X-Pol formed of a solid substrate 1 covered with a single layer 2 in the general case where the support, the layer 2, and the incident medium 3 have any complex optical indices (possibly absorbent media).

VI.2-1) Ideal Supports AR-X-Pol-1

Among these, the ideal supports for the angle $\theta_0$ are obtained when $\sigma=0$, where the quantity $\sigma$ is given by the equation E19, where $\beta_1$ is linked with the angle $\theta_1$ by the relation E18, $\theta_2$, $\theta_1$ and $\theta_0$ being always linked with the Snell relation extended to the complex functions.

The equation:

$$\sigma_{01} + \sigma_{12}(1+\pi_{01})z + \sigma_{01}\pi_{12}z^2 = 0 \quad \text{(E19 ter)}$$

always has 2 solutions $z_1$ and $z_2$ arranged according to their modulus, $|z_1| < |z_2|$, which are expressed in relation to the coefficients $\sigma_{01}$, $\sigma_{12}$, $\pi_{01}$ and $\pi_{12}$ themselves in relation to the three indices $n_0$, $n_1$, $n_2$ and to the angle $\theta_0$. The medium 1 not being amplifying, the solution $z_1$ is the sole acceptable. Its expression translates by a relation which defines digitally the family of the ideal supports AR-X-POL-1. This family is delineated by the condition $|z_1| \leq 1$.

VI.2-2) Approximate Supports AR-X-Pol-1.

When the three indices are imposed or constrained and one of them at least is complex, the minimum of $|\sigma|$ with respect to $e_1$ is not zero any longer if the condition E42 is not verified by the solution of smaller modulus of the equation E19ter, but it exists nevertheless since $|\sigma|$ is a quasi-periodic function of $e_1$. By "quasi-periodic" is meant here that $n_1$ being complex, the modulus of $e^{-4j\beta_1}$ is dampened when $e_1$ increases.

The best possible extinction coefficient taking the constraints into account is obtained by looking for the minimum of $|\sigma|$ (or similarly that of $|\sigma|^2$) with respect to $e_1$. At $\theta_1$ and $n_1$ fixed, this amounts to looking for it with respect to the complex quantity $\beta_1$, which may be done numerically.

The thickness $e_1$ is then given by the equation:

$$e_1 = \frac{\lambda \beta_1}{2\pi |n_1 \cos\theta_1|} \quad \text{(E43)}$$

which is a generalisation of the equation E18.

VI.2-3) Ideal Dielectric Coating on Absorbent Support.

A useful particular case is that where only the support is absorbent, the indices of the other media remaining real. Then $\beta_1$ is real, and $|\sigma|$ is a periodic function of $\beta_1$.

But as $\sigma_{12}$ and $\pi_{12}$ are complex, $e^{-2j\beta_1}$ is not real. The optimal thickness which negates $|\sigma|$ is therefore given by:

$$n_1 e_1 \cos\theta_1 = e_c + k\frac{\lambda}{2} \quad \text{(E44)}$$

where the smallest of the solutions $e_c$ is not equal to $\lambda/4$ nor to $\lambda/2$ any longer.

This equation generalises the equations E24 and E25.

Thus, in the case of a substrate 1 absorb, the coating AR-X-POL differs from a conventional antiglare coating, not only by its index, but also by its thickness.

VII. Ideal Contrast Amplifying Supports

For visualising the edge of a study object having the form of a thin film placed on the surface of the support, it is advisable to exploit the difference between the intensities collected on the one hand while observing the film and on the other hand while observing the bare surface of the substrate 1 which are noted $I_F$ and $I_S$ (or similarly I(F) and I(S)). These intensities are proportional to the corresponding standardised intensities.

The contrast of the edge of the film is given by the following relation:

$$C_f = \frac{I_F - I_S}{I_F + I_S} \quad \text{(E50)}$$

$I_F$ and $I_S$ being positive, $C_f$ is a strictly increasing function of the ratio $I_F/I_S$.

To visualise the film correctly, $|C_f|$ should be maximised and therefore the ratio $I_F/I_S$ should be made maximal ($I_S \to 0$, to tend towards a contrast of 1) or minimal ($I_F \to 0$, to tend towards a contrast of $-1$). Therefore, either the surface or the film should be extinguished.

A sensitive visualisation process lies on the one hand on a good extinction, and on the other hand on a critical extinction, i.e. very sensitive to the thickness of the last layer 2 of the stack. The antiglare supports AR-X-Pol exhibit these qualities and are therefore also contrast amplifying supports.

The performances of a visualisation process may be quantified by the contrast obtained when the film observed becomes extremely thin. In this case, $I_F$ and $I_S$ become neighbours and $dI=I_F-I_S$ is close to a differential element.

For a film of very small thickness $\Delta e$ placed on the support, one may write in the first order in $\Delta e$:

$$\frac{I_F}{I_S} = 1 + \frac{1}{I_S}\frac{dI}{de}\Delta e \quad \text{(E51)}$$

$$\approx 1 + \Delta e \frac{d}{de} \ln I$$

where it has been assumed that optical index of the film is identical to that of the upper layer 2, i.e. of the last layer 2 of the stack, and where dI/de is the derivate of the intensity reflected by the bare substrate 1 with respect to the thickness e of this layer 2.

In the case where the substrate 1 is composed of a solid support covered with a single dielectric layer 2, e is therefore the thickness of the single layer 2. The film appears therefore as a simple fluctuation of thickness of the upper layer 2.

An optimal contrast is therefore obtained for both situations:

i) $\frac{d}{de} \ln I \rightarrow +\infty$ (extinction of the support, $C_f = +1$)

ii) $\frac{d}{de} \ln I = -1$ (extinction of the film, $C_f = -1$)

The optimal contrast may only be reached with a total extinction.

The sensitivity of the visualisation is, in Angströms$^{-1}$:

$$\frac{C_f}{\Delta e} = \frac{1}{2} \frac{d \ln I}{de} \quad (E52)$$

It has a meaning only when the contrast is small (when $$\frac{d \ln I}{de} \Delta e$$

is very small compared to 1) and enables to compare detection thresholds.

VII. 1) In Non-Polarised Light

In the equation E51, $$\frac{I_F}{I_S} = \frac{R_{NP}(F)}{R_{NP}(S)} \approx 1 + \Delta e \frac{d}{de} \ln R_{NP}.$$

Since the total extinction is only possible with a perfect antiglare support and since this support only exists for a normal incidence, the performances of this support for convergent light visualisation, i.e. for imaging purposes, are limited.

VII. 2) Between Crossed Polariser and Analyser

The equation E51 becomes:

$$\frac{R_F(\phi)}{R_S(\phi)} \approx 1 + \Delta e \frac{d}{de} \ln|\sigma|^2 \quad (E52)$$

An optimal contrast is therefore obtained for both situations:

i) $\frac{d}{de} \ln|\sigma|^2 \rightarrow +\infty$ (extinction of the support, $C_f = +1$)

ii) $\frac{d}{de} \ln|\sigma|^2 = -1$ (extinction of the film, $C_f = -1$)

Each of these situations corresponds to σ=0 i.e. at an ideal support AR-X-Pol. In the first equation, the optimal thickness e is that of the coating on its own. In the second equation, it is the sum of the thicknesses of the coating and of the object.

The sensitivity of the visualisation is given by, in [Angströms$^{-1}$]:

$$\frac{C_F}{\Delta e} = \frac{d}{de} \ln|r_p + r_s|$$

There results from the previous considerations that:
1) the best contrast amplifying supports are the ideal antiglare supports.
2) the supports AR-X-Pol are the single supports capable of providing total extinction in annular illumination and a quasi-perfect extinction with little convergent illumination. The use of these supports between crossed polarisers enables to obtain noticeably better contrasts than all other supports in all the imaging modes without labelling using incoherent illumination.

VIII. Non Ideal Contrast Amplifying Supports in Polarised Light:

VIII.1) Between Crossed Polarisers

When the support is not ideal any longer, the equation E19 bis is not satisfied any longer. It is in particular the case when the index of the layer 2 is imposed and it has no solution any longer because the relation E26 is not verified any longer. Then, the total extinction is not possible any longer and the condition $C_f=+1$ may not be reached any longer (the condition $C_f=-1$ may still be possible for a very particular object). We show that the contrast is not optimised any longer when the minimum of the reflected intensity is reached, but for thicknesses of layer 2 situated on both sides of this minimum, the minimum corresponding to the sign inversion of the contrast.

In this case, the contrast is optimised when:

i) $\frac{d}{de} \ln|\sigma|^2$ maximum (partial extinction of the support, $C_f$ maximum)

ii) $\frac{d}{de} \ln|\sigma|^2$ minimum (partial extinction of the film, $C_f$ minimum)

I.e. when:

$$\frac{d^2}{de^2} \ln|\sigma|^2 = 0 \quad (E57)$$

We shall limit ourselves to the case of dielectric materials and we are looking for the optimal thickness of the dielectric layer 2 for optimising the contrast with an amplifying coating made of a single layer 2.

The thickness of contrast inversion $e_1$ is given by the equation E24 which corresponds to the condition that $e^{-2/\beta_1}$ is real. In order to explore the thicknesses situated on both sides of $e_1$, we assume $$\beta_1 = \frac{\pi}{2} + \varepsilon.$$

As the relation E26 is not completely verified any longer, we assume:

$$\Delta \equiv \frac{\sigma_{12}(1+\pi_{01}) - \sigma_{01}(1+\pi_{12})}{\sigma_{01}} \quad \text{(E58)}$$

The development in $\varepsilon$ of $|\sigma|^2$ gives:

$$|\sigma|^2 = \sigma_{01}^2 \left(\frac{A + 4B\varepsilon^2}{C + 4D\varepsilon^2}\right) \quad \text{(E59)}$$

an expression wherein:

$$A = \Delta^2 \quad \text{(E60)}$$

$$B = (1-\pi_{12})^2 + \Delta(1+\pi_{12}) \quad C = (1-P+\pi_{01}\pi_{12}) \quad D = P + P\pi_{01}\pi_{12} - 4\pi_{01}\pi_{12}$$

and where:

$$P = r_{01(p)} r_{12(p)} + r_{01(s)} r_{12(s)} \quad \text{(E61)}$$

There follows:

$$\frac{d}{d\varepsilon} \ln|\sigma^2| = \frac{8B\varepsilon}{A + B\varepsilon^2} - \frac{8D\varepsilon}{C + D\varepsilon^2} \quad \text{(E61)}$$

The solution of the equation E57 is:

$$4\varepsilon^2 = \frac{AC}{BC + AD} \quad \text{(E62)}$$

If the coating remains up to scratch, $\Delta$ is small, and in such a case $\varepsilon$ is close to $\Delta/2$.

The relation of definition E18 provides finally with both thicknesses $e_1'$ and $e_1''$ which optimise the contrast:

$$e_1' = \frac{\lambda}{4}\left(1 + \frac{2\varepsilon}{\pi}\right) + k\frac{\lambda}{2} \quad \text{(E63)}$$

$$e_1'' = \frac{\lambda}{4}\left(1 - \frac{2\varepsilon}{\pi}\right) + k\frac{\lambda}{2}$$

The formulas E63 generalise the formula E24 to the non ideal contrast amplifying supports.

We shall designate the family of the contrast amplifying supports by the designation supports Ampli-Pol when it is advisable to differentiate it from the supports AR-Pol. Between crossed polarisers, they become the supports Ampli-X-Pol, etc.

IX. Anisotropic Supports AR-X-Pol and Ampli-X-Pol

In any use of a support AR-Pol or of a support Ampli-Pol, it is essential to optimise its performances (useful extinction rate $C_u$ or contrast $C_f$). To do so, one should comply with the relations which define it with precision, which generates difficulties of manufacture (strict tolerance on the thickness e for example) and difficulties of implementation (adjustment of the parameters of the microscope for visualisation for instance).

In order to remedy these difficulties, it is advantageous to introduce in the supports an adjustment element. This element is provided by the use of materials with anisotropic optical properties in the realisation of the supports. By default, the anisotropic material is the substrate 1, the layer 2 and the incident medium remaining isotropic. The main axes (x, y, and z) of the anisotropic material are parallel and perpendicular to the surface of the support. The Fresnel coefficients of the support are replaced with a reflection matrix:

$$\begin{pmatrix} r_{pp} & r_{ps} \\ r_{sp} & r_{ss} \end{pmatrix} \quad \text{(E70)}$$

wherein, taking into account, the orientations of the main axes $r_{ps} = r_{sp} = 0$, which enables to express the reflected amplitude relative to the incident amplitude as:

$$\begin{pmatrix} E_{r_p} \\ E_{r_s} \end{pmatrix} = \begin{pmatrix} r_{px} & 0 \\ 0 & r_{sx} \end{pmatrix} \begin{pmatrix} E_{ip} \\ E_{is} \end{pmatrix} \quad \text{(E71)}$$

when the axis x is in the plane of incidence, and as:

$$\begin{pmatrix} E_{r_p} \\ E_{r_s} \end{pmatrix} = \begin{pmatrix} r_{py} & 0 \\ 0 & r_{sy} \end{pmatrix} \begin{pmatrix} E_{ip} \\ E_{is} \end{pmatrix} \quad \text{(E71)}$$

when the y axis is in the plane of incidence. At the interface between the isotropic medium i and the anisotropic medium j, the coefficients $r_{ij(px)}$, $r_{ij(sx)}$, $r_{ij(py)}$ and $r_{ij(sy)}$ are given by $$r_{ij(px)} = \frac{n_{jx} n_{jz} c_i - n_i (n_{jz}^2 - n_i^2 s_i^2)^{\frac{1}{2}}}{n_{jx} n_{jz} c_i + n_i (n_{jz}^2 - n_i^2 s_i^2)^{\frac{1}{2}}} \quad \text{(E72)}$$

$$r_{ij(sx)} = \frac{n_i c_i - (n_{jy}^2 - n_i^2 s_i^2)^{\frac{1}{2}}}{n_i c_i + (n_{jy}^2 - n_i^2 s_i^2)^{\frac{1}{2}}}$$

if the plane of incidence is parallel to x, and:

$$r_{ij(py)} = \frac{n_{jy} n_{jz} c_i - n_i (n_{jz}^2 - n_i^2 s_i^2)^{\frac{1}{2}}}{n_{jy} n_{jz} c_i + n_i (n_{jz}^2 - n_i^2 s_i^2)^{\frac{1}{2}}} \quad \text{(E73)}$$

$$r_{ij(sy)} = \frac{n_i c_i - (n_{jx}^2 - n_i^2 s_i^2)^{\frac{1}{2}}}{n_i c_i + (n_{jx}^2 - n_i^2 s_i^2)^{\frac{1}{2}}}$$

if the plane of incidence is parallel to y.

The equations E72 show that, according to the relative orientation Φ=(P,x) of the sample and of the polariser P in azimuth, obtaining by rotating one element with respect to the other around the normal, one obtains variable effective Fresnel coefficients $r_{ij(p)}$ and $r_{ij(s)}$, given by the following linear combinations:

$$r_{ij(p)} = r_{ij(px)} \cos \phi + r_{ij(py)} \sin \phi \quad (E74)$$

$$r_{ij(s)} = r_{ij(sx)} \cos \phi + r_{ij(sy)} \sin \phi$$

An analogue reasoning applies to the case where the substrate 1 is isotropic and the layer 2 anisotropic.

Thus, a support optimal for visualisation under microscope in polarised light is anisotropic and such that the optimal value of its reflection coefficients $r_p$ and $r_s$ is obtained for an intermediate angle Φ between 0 and π/2 and preferably equal to π/4 to provide maximum freedom of adjustment.

X. Circular Polarisation

The invention may not be limited to the foregoing description. The light beam used has thus, in another embodiment a circular polarisation and the supports AR-Pol and Ampli-Pol exhibit advantageously the same efficiency. As it is well known, the observations and measurements between crossed polariser and analyser are then replaced with equivalent observations and measurements between [polariser followed by a ¼ wave plate] and [identical ¼ wave plate followed by a polariser (or analyser) parallel to the former, preferably identical]. This is also valid for all the techniques of visualisation and of measurement using differential interferential contrast (DIC).

The support of the invention has been subject to several implementations presented in the following examples for which the random illumination wavelength is, unless otherwise specified, λ=540 nm.

It has been observed that when a support complying with the invention has been determined, it is possible to deduce therefrom other supports which, from the invention viewpoint, have comparable properties by modifying the thickness $e_1$ of the layer 2 and the length λ of use while maintaining their ratio $e_1/\lambda$ constant. This opens very wide possibilities.

EXAMPLE 1

The supports AR-Pol, although obeying very stringent construction rules, can be varied endlessly. Four examples (index $n_1$ and thickness of layer $e_1$(Å)) of supports AR-Pol-1 ideal for an incidence close to the normal ($\theta_0=5°$) are presented below. These examples are intended for use as object-carrying supports for observations and measurements conducted in a surrounding medium such as air (the incident medium being the air or the substrate).

| Substrate | $n_2$ | $n_1$ | $e_1$(Å) |
|---|---|---|---|
| Gold | 0.40-2.6j | 1.70 | 694 |
| Silver | 0.13-3.44j | 1.59 | 795 |
| Aluminium | 0.92-0.95j | 2.01 | 346 |
| Nickel | 1.76-3.2j | 1.51 | 847 |

We also give for these substrates 1 the indices $n_1$ and the thicknesses $e_1$ of the single layer 2 coatings which optimise the contrast $C_f$ of any observation between crossed polarisers with a convergent axial illumination under an incidence of 0.2° (by convention $\theta_o=0$) and we give the value $n_1$ and the absolute value of the contrast $C_f$ obtained with convergent illumination with 30° opening at the edge of a film with 1 nanometer thickness as well as the thicknesses $e_1'$ and $e_1''$ as defined by the equations 63.

The index $n_2$ is the index of the material forming the support. It is extracted from <<Hand Book of Optics, Mc Graw Hill Professional Publishing New York 2000>> wherein a particular wavelength is defined for each material.

| Substrate | $n_2$ | $\theta_0=0$ $n_1$ | $\theta_0=0$ $e_1$(Å) | $C_f$ | $0<\theta_0<\frac{\pi}{6}$ $n_1$ | $0<\theta_0<\frac{\pi}{6}$ $e_1'$(Å) | $0<\theta_0<\frac{\pi}{6}$ $e_1''$(Å) | $C_f$ |
|---|---|---|---|---|---|---|---|---|
| Gold | 0.47 – 2.83j | 1.65 | 800 | 1 | 1.58 | 870 | 880 | 0.17 |
| Silver | 0.2 – 3.44j | 1.60 | 850 | 1 | 1.53 | 930 | 940 | 0.17 |
| Aluminium | 1.44 + 5.23j | 1.50 | 953 | 1 | 1.44 | 1040 | 1050 | 0.07 |
| Nickel | 1.58 – 3.42j | 1.52 | 920 | 1 | 1.46 | 1000 | 1010 | 0.06 |

Besides, we also give, for these substrates 1, the indices $n_1$, thicknesses $e_1$ of the single layer 2 coatings which optimise the contrast $C_f$ of any observation between crossed polarisers with annular illumination under an incidence of 20°. We give the absolute value of the contrast $C_f$ obtained under these conditions, with convergent illumination with 30° opening (π/6) at the edge of a film with 1 nanometer thickness. The thicknesses $e_1'$ and $e_1''$ are those given by the equations E63.

| Substrate | $n_2$ | $\theta_0=20°$ $n_1$ | $\theta_0=20°$ $e_1$(Å) | $C_f$ | $0<\theta_0<\frac{\pi}{6}$ $n_1$ | $0<\theta_0<\frac{\pi}{6}$ $e_1'$(Å) | $0<\theta_0<\frac{\pi}{6}$ $e_1''$(Å) | $C_f$ |
|---|---|---|---|---|---|---|---|---|
| Gold | 0.40 – 2.6j | 1.64 | 739 | 1 | 1.64 | 730 | 740 | 0.65 |
| Silver | 0.13 – 3.44j | 1.55 | 838 | 1 | 1.55 | 832 | 842 | 0.85 |

-continued

| Substrate | $n_2$ | $\theta_0 = 20°$ $n_1$ | $\theta_0 = 20°$ $e_1(Å)$ | $C_f$ | $0 < \theta_0 < \frac{\pi}{6}$ $n_1$ | $0 < \theta_0 < \frac{\pi}{6}$ $e_1'(Å)$ | $0 < \theta_0 < \frac{\pi}{6}$ $e_1''(Å)$ | $C_f$ |
|---|---|---|---|---|---|---|---|---|
| Aluminium | 0.92 − 0.95j | 1.89 | 399 | 1 | 1.89 | 395 | 415 | 0.25 |
| Nickel | 1.76 − 3.2j | 1.48 | 890 | 1 | 1.48 | 880 | 905 | 0.50 |

The indices $n_1$ are very common and the layers 2 may be realised by all the conventional deposition techniques, for example oxide depositions realised by PECVD (Phase evaporation chemical vapour deposition).

EXAMPLE 2

Examples (index $n_1$) of supports AR-Pol-1 are presented below for a substrate 1 of silicium and for uses either in a surrounding medium such as air, or in immersion.

Ideal anisotropic supports AR-Pol may be obtained by depositing on a substrate 1 of silicium ($n_2$=4.12−0.05j) doped or not, cleaved according to a plane 100, a layer 2 of optical thickness $\lambda/4$ according to the relation E24 and of index $n_1$ equal to:
1.37 when the incident medium is air (index 1)
1.79 when the incident medium is water (index 1.33)
1.99 when the incident medium is oil (index 1.5).

The layers 2 then have less common indices which are obtained preferably:
   either by sol-gel and aerogel process leading to porous silicas (index 1.37), the index also being approximated correctly by a layer of $MgF_2$ (index 1.38).
   or by oxidation techniques with gas mixtures leading to material mixtures $SiO_2$—SiO (index 1.79), or to oxinitride layers $SiO_xN_y$ (indices 1.79 and 1.99) with the following proportions: x=0.4 and y=0.6 to obtain $n_1$=1.79; x=0 and y=1 to obtain $n_1$=1.99.

The index $n_1$=1.37 may also be obtained by depositing fluorinated polymers (such as trifluoroalkyl-alkylsiloxanes or trifluoroalkyl-alkylsiloxane and dimethylsiloxane copolymers), whereas the deposition may be conducted by spin-coating from a solution.

These indices 1.79 and 1.99 may also be obtained by all the deposition techniques, in particular by PECVD deposition of oxide mixtures such as $HfO_2$ and $Y_2O_3$ or of all the materials listed in the dictionaries of physical properties of the materials (for example: Handbook of Optical constants of solids, Vol. 1-5, Academic Press, Ed. Palik and Ghosh (1997)) or in the optics dictionaries (for example: Handbook of optics, McGraw-Hill Professional Publishing, New-York, (2000)).

The index of certain materials changes significantly with the wavelength of the light, and the adjustment of index may be replaced with an adjustment of wavelength; it is for example the case of a layer 2 of SiO which exhibits a useful index of 1.95 for $\lambda$=490 nm and of 1.99 for $\lambda$=540 nm.

EXAMPLE 3

We give below a few other examples of ideal supports AR-Pol (which are therefore also ideal Ampli-Pol) for different incident media and for an annular illumination of very small incidence ($\theta_o$=5 degrees). The thickness $e_1$ is in Angstroms.

A first table is given for an angle of incidence of 0.2°. The index $n_2$ is the index of the material forming the support. It is extracted from «Hand Book of Optics, Mc Graw Hill Professional Publishing New York 2000 wherein a particular wavelength is defined for each material.

| Substrate | $n_2$ | $n_0$ | $n_1$ | $e_1$ |
|---|---|---|---|---|
| Gold | 0.47-2.83j | 1.33 | 2.42 | 490 |
| Gold | | 1.5 | 2.95 | 368 |
| Silver | 2.0-3.44j | 1.33 | 2.35 | 526 |
| Silver | | 1.5 | 2.8 | 417 |
| Aluminium | 1.44 + 5.23j | 1.33 | 2.05 | 684 |
| Aluminium | | 1.5 | 2.33 | 587 |
| Nickel | 1.58-3.42j | 1.33 | 2.13 | 620 |
| Nickel | | 1.5 | 2.5 | 505 |
| Cadmium | 1.13-5.01j | 1 | 1.47 | 968 |
| Cadmium | | 1.33 | 2.08 | 667 |
| Cadmium | | 1.5 | 2.38 | 575 |
| Tin | 1.43-5.25j | 1 | 1.48 | 975 |
| Tin | 1.48-5.25j | 1 | 1.48 | 975 |
| | | 1.33 | 2.03 | 693 |
| | | 1.5 | 2.34 | 600 |
| copper | 0.52-2.57j | 1 | 1.68 | 768 |
| copper | | 1.33 | 2.52 | 448 |
| copper | | 1.5 | 3.05 | 338 |
| Iron (evaporated) | 1.51-1.63j | 1 | 1.545 | 802 |
| | | 1.33 | 2.24 | 459 |
| | | 1.5 | 2.72 | 332 |

A second table is given for an angle of incidence of 5°.

The wavelength is $\lambda$=540 nm except for the Cadmium where it is equal to 589.3 nm.

| Substrate | $n_2$ | $n_0$ | $n_1$ | $e_1$ |
|---|---|---|---|---|
| Gold | 0.40-2.6j | 1.33 | 2.42 | 490 |
| Gold | 0.40-2.6j | 1.5 | 1.79 | 755 |
| Silver | 0.13-3.44j | 1.33 | 2.28 | 512 |
| Silver | 0.13-3.44j | 1.5 | 2.7 | 412 |
| Aluminium | 0.92-0.95j | 1 | 1.89 | 399 |
| Nickel | 1.76-3.2j | 1.33 | 2.11 | 572 |
| Nickel | 1.76-3.2j | 1.5 | 2.45 | 473 |
| Cadmium | 1.13-5.01j | 1 | 1.49 | 970 |
| Cadmium | 1.13-5.01j | 1.33 | 2.05 | 684 |
| Cadmium | 1.13-5.01j | 1.5 | 2.36 | 582 |
| Tin | 1.48-5.25j | 1 | 1.48 | 899 |
| Tin | 1.48-5.25j | 1.33 | 2.02 | 640 |
| Tin | 1.48-5.25j | 1.5 | 2.33 | 548 |
| Copper | 1.04-2.59j | 1 | 1.62 | 746 |
| Copper | 1.04-2.59j | 1.33 | 2.23 | 423 |
| Copper | 1.04-2.59j | 1.5 | 2.83 | 351 |
| Iron (evaporated) | 1.51-1.63j | 1 | 1.54 | 737 |
| Iron (evaporated) | 1.51-1.63j | 1.33 | 2.23 | 423 |
| Iron (evaporated) | 1.51-1.63j | 1.5 | 2.72 | 305 |

EXAMPLE 4

Finally, we give an example with an annular illumination at a wavelength $\lambda$=589.3 nm and a significant angle of incidence. For a support of cadmium 10 and observation in a surrounding medium such as air under a single angle of incidence of 30 degrees, the ideal layer 2 is obtained for $n_1=1.42$ and $e_1=1084$ Angströms.

The values of the indices are deduced from the book of Born and Wolf, entitled "Principles of Optics: Electromagnetic Theory of Propagation, Interference and diffraction of Light", Cambridge University Press (1999) and from the book of E. D. Palik, entitled <<Handbook of optical constants of solids>>, vol. 1 to 5, Academic Press (1985).

Applications are possible in the industries of the optics, for improving measurements or the reflection-based observation of thin films or very small objects under optical microscope or under any other optical imaging instrument such as visor, spectacles, macroscope, magnifying glass, binocular magnifying glass, camera, photo camera, near field microscope, endoscope, optical near field microscope, biochip reader, magneto-optical reader, confocal microscope.

The supports AR-X-Pol and Ampli-Pol are usable simultaneously as antiglare background and as object-carrying support for all microscopy operation in reflection polarised light, regardless whether the observation is conducted in open air, in immersion, or through the support.

They enable optimal visualisation not only of objects placed on the surface of the support, but also of the interface between the substrate 1 and the layer 2.

They enable optimal visualisation and measurement of all the effects of dichroism and of birefringence inside the layer 2 properly speaking.

This is particularly advantageous for parallel imaging and reading of magnetic fields situated in the layer when it possesses magneto-optic susceptibility at each of the following effects: Faraday effect, Voigt effect, linear magnetic birefringence.

They enable optimal visualisation and measurement of all the reflection anisotropic effects at the interface between the substrate 1 and the layer 2, which is particularly advantageous for implementing the anisotropic reflection microscopy technique (RAM).

This is also particularly advantageous if the substrate 1 exhibits magneto-optic susceptibility (longitudinal or transverse Kerr effect, polar Kerr effect), the coatings AR-Pol providing considerable improvement in contrast and in sensitivity of the magneto-optic reading process.

The supports AR-Pol are particularly efficient for reflection differential interferential contrast observations, regardless of the variation of the technique used, and regardless of the type of polarisation used (linear or circular) and enable the combination of all these interferential contrast techniques with all the other visualisation, detection or measurement techniques mentioned above.

The single layer 2 coatings AR-Pol exist for all the types of substrates 1. They enable more sensitive detection than with all the other modification techniques which take place at the end of an optic fibre, and notably the detection of a species captured by a sensitive layer 2 installed at the end of such a fibre.

These are ideal object-carrying supports for near field microscopy techniques (AFM, STM, SNOM, and other SPM) since they enable detection, localisation and visualisation of films or objects invisibles by conventional optical techniques.

These are also ideal supports to conduct in situ optical tracking or to control a posteriori the depositions of ultra thin layers 2 performed by all the deposition techniques available, for example by the Langmuir-Blodgett technique, by plasma, ionic deposition, spin-coating, dip-coating, MBE techniques, etc. . . .

Used as object-carrying supports, they also increase the efficiency of magneto-optic techniques, polarised light cofocal microscopy techniques, SNOM techniques (Scanning Near-field Optical Microscopy) in polarised light, and of all the spectroscopic visualisation techniques (Infrared Absorption, Raman, Fluorescence, ultra-violet Absorption, 2-photon Microscopy).

Used as object-carrying supports, they enable to increase considerably the quality of reflectivity measurements in polarised light and of ellipsometry under optical microscope.

The supports AR-Pol are also advantageously used as object-carrying supports in all the micro-manipulation devices under optical microscope: optical tweezers, magnetic tweezers, piezoelectric tweezers.

The invention claimed is:

1. A support intended for observing between crossed polarisers an object placed on the support or in the vicinity thereof in a medium (3) of refraction index $n_0$ with spatially incident convergent spatially incoherent illumination under an angle $\theta_0$ at a wavelength $\lambda$, including a substrate (1) of complex refraction index $n_2$, and a layer (2) of complex refraction index $n_1$ and of thickness $e_1$ on said substrate, said substrate and said layer being in a medium of index $n_0$ and being configured for observation with spatially incident convergent non-coherent illumination under an angle $\theta_0$ at a wavelength $\lambda$, said angle $\theta_0$ being with respect to and axis normal to an observation surface of the support wherein, the value of the thickness $e_1$ of the layer (2) is within 2% so that:

$$\frac{d^2}{de_1^2}\ln|\sigma|^2 = 0$$

with $$\sigma = \frac{\sigma_{01} + \sigma_{12}(1+\pi_{01})e^{(-2j\beta_1)} + \sigma_{01}\pi_{12}e^{(-4j\beta_1)}}{(1 + r_{01(p)}r_{12(p)}e^{(-2j\beta_1)})(1 + r_{01(s)}r_{12(s)}e^{(-2j\beta_1)})}$$

a formula wherein $\sigma_{ik}$ and $\pi_{ik}$ represent respectively the sum and the product of the Fresnel coefficients of the different interfaces [(i,k)=(0,1) or (1,2)]

$$r_{ik(p)} = \frac{n_k\cos\theta_i - n_i\cos\theta_j}{n_k\cos\theta_i + n_i\cos\theta_k}$$

and $$r_{ik(s)} = \frac{n_i\cos\theta_i - n_k\cos\theta_k}{n_i\cos\theta_i + n_k\cos\theta_k}$$

and wherein $\beta_1 = \frac{2\pi n_1 e_1 \cos\theta_1}{\lambda}$, with $\cos\theta_1 = \sqrt{1 - \left(\frac{n_0}{n_1}\right)^2 \sin^2\theta_0}$.

2. A support according to claim 1, intended for use with annular incident illumination with an angle of incidence $\theta_0$ which is unique within $\pm 2.5°$.

3. A support according to claim 1, configured for use in incident and convergent axial illumination with an average angle of incidence $\theta_0$ associated with a total angular opening $\Delta\theta_0$ by the relation:

$$\cos\theta_0 = \cos^2\left(\frac{\Delta\theta_0}{2}\right).$$

4. A support according to claim 1, characterised in that the illumination is monochromatic or quasi-monochromatic at the wavelength λ.

5. A support according to claim 1, characterised in that the illumination has a continuous wide spectrum or is polychromatic with maximum span ±0.3 λ around its average wavelength λ.

6. A support according to claim 1, intended for use in the air as a surrounding medium (3), with $\theta_0$=30° and λ=589.3 nm, characterised in that the substrate (1) is made of cadmium with $n_2$=1.13-5.01j, the layer (2) having an index $n_1$=1.42 and $e_1$=1084 Angströms.

7. A support according to claim 1, characterised in that the substrate (1) and the layer (2) have the specificities of the following table wherein $n_1$ and $e_1$ are the index and the thickness of the layer, $n_2$ the complex refraction index of the substrate (1), in the air as a surrounding medium (3), $\theta_0$=5° and λ=540 nm

| Substrate | $n_2$ | $n_1$ | $e_1$ (Å) |
|---|---|---|---|
| Gold | 0.40-2.6j | 1.70 | 694 |
| Silver | 0.13-3.44j | 1.59 | 795 |
| Aluminium | 0.92-0.95j | 2.01 | 346 |
| Nickel | 1.76-3.2j | 1.51 | 847. |

8. A support according to claim 1, characterised in that $\theta_0$ is an average angle of incidence equal to 20° and in that the substrate (1) and the layer (2) have the specificities of the following table wherein $n_1$ and $e_1$ are the index and the thickness of the layer (2), $n_2$ the complex refraction index of the substrate (1), in the air as a surrounding medium (3) and λ=540 nm

| Substrate | $n_2$ | $n_1$ | $e_1$ (Å) |
|---|---|---|---|
| Gold | 0.40-2.6j | 1.64 | 739 |
| Silver | 0.13-3.44j | 1.55 | 838 |
| Aluminium | 0.92-0.95j | 1.89 | 399 |
| Nickel | 1.76-3.2j | 1.48 | 890. |

9. A support according to claim 1, characterised in that $\theta_0$ is equal to 5° and in that the substrate (1) and the layer (2) have the specificities of the following table wherein $n_1$ and $e_1$ are the index and the thickness of the layer (2) within 2%, $n_2$ the complex refraction index of the substrate (1), $n_0$ the index of the surrounding medium (3), λ=589,3 nm when the substrate is made of cadmium and λ=540 nm in the other cases

| Substrate | $n_2$ | $n_0$ | $n_1$ | $e_1$ |
|---|---|---|---|---|
| Gold | 0.40-2.6j | 1.33 | 2.42 | 490 |
| Gold | 0.40-2.6j | 1.5 | 1.79 | 755 |
| Silver | 0.13-3.44j | 1.33 | 2.28 | 512 |
| Silver | 0.13-3.44j | 1.5 | 2.7 | 412 |
| Aluminium | 0.92-0.95j | 1 | 1.89 | 399 |
| Nickel | 1.76-3.2j | 1.33 | 2.11 | 572 |
| Nickel | 1.76-3.2j | 1.5 | 2.45 | 473 |
| Cadmium | 1.13-5.01j | 1 | 1.49 | 970 |
| Cadmium | 1.13-5.01j | 1.33 | 2.05 | 684 |
| Cadmium | 1.13-5.01j | 1.5 | 2.36 | 582 |
| Tin | 1.48-5.25j | 1 | 1.48 | 899 |
| Tin | 1.48-5.25j | 1.33 | 2.02 | 640 |
| Tin | 1.48-5.25j | 1.5 | 2.33 | 548 |
| Copper | 1.04-2.59j | 1 | 1.62 | 746 |
| Copper | 1.04-2.59j | 1.33 | 2.23 | 423 |
| Copper | 1.04-2.59j | 1.5 | 2.83 | 351 |
| Iron (evaporated) | 1.51-1.63j | 1 | 1.54 | 737 |
| | 1.51-1.63j | 1.33 | 2.23 | 423 |
| | 1.51-1.63j | 1.5 | 2.72 | 305. |

10. A support according to claim 1, characterised in that the parameters are kept with the exception of the wavelength λ and of the thickness $e_1$ of the layer 2 which are modified proportionally, $e_1/\lambda$ not being modified.

11. An accessory configured for observing a liquid sample, said accessory being formed of a Petri dish and of a support configured to receive said sample, wherein
the support complies with claim 1,
the support is a bottom of the Petri dish.

12. A device for observing a sample including an optical microscope, an accessory intended for receiving said sample, a polariser and a quarter-wave plate, characterised in that the accessory complies with claim 11.

13. A device for observing a sample including an optical microscope, a support intended for receiving said sample and two crossed polarisers, characterised in that the support complies with claim 1.

14. A device for observing a sample including an optical microscope, an accessory intended for receiving said sample and two crossed polarisers, characterised in that the accessory complies with claim 11.

15. A device for observing a sample according to claim 13, characterised in that the optical microscope is fitted with a differential interferential contrast device.

16. A device for observing a sample including an optical microscope, a support intended for receiving said sample, a polariser and a quarter-wave plate, characterised in that the support complies with claim 1.

17. A support intended for observing between crossed polarisers an object placed on the support or in the vicinity thereof in a medium (3) of refraction index $n_0$ with incident convergent spatially incoherent illumination under an angle $\theta_0$ at a wavelength λ, including
a substrate (1) of complex refraction index $n_2$,
a layer (2) of complex refraction index $n_1$ and of thickness $e_1$ on said substrate, said substrate and said layer being in a medium of index $n_0$ and being configured for observation with spatially incident convergent non-coherent illumination under an angle $\theta_0$ at a wavelength λ, said angle $\theta_0$ being with respect to and axis normal to an observation surface of the support
wherein,
the value of the thickness $e_1$ of the layer (2) is within 2% so that:

$$\frac{d}{de_1}|\sigma^2| = 0$$

with

-continued $$\sigma = \frac{\sigma_{01} + \sigma_{12}(1+\pi_{01})e^{(-2j\beta_1)} + \sigma_{01}\pi_{12}e^{(-4j\beta_1)}}{(1+r_{01(p)}r_{12(p)}e^{(-2j\beta_1)})(1+r_{01(s)}r_{12(s)}e^{(-2j\beta_1)})}$$

a formula wherein $\sigma_{ik}$ and $\pi_{ik}$ represent respectively the sum and the product of the Fresnel coefficients of the different interfaces [(i,k)=(0,1) or (1,2)]

$$r_{ik(p)} = \frac{n_k\cos\theta_i - n_i\cos\theta_j}{n_k\cos\theta_i + n_i\cos\theta_k}$$

and $$r_{ik(s)} = \frac{n_i\cos\theta_i - n_k\cos\theta_k}{n_i\cos\theta_i + n_k\cos\theta_k}$$

and wherein $\beta_1 = \frac{2\pi n_1 e_1 \cos\theta_1}{\lambda}$, with $\cos\theta_1 = \sqrt{1 - \left(\frac{n_0}{n_1}\right)^2 \sin^2\theta_0}$.

18. A support according to claim 17, characterised in that the values of the refraction index $n_1$ and of the thickness $e_1$ of the layer (2) are within 2% such that:

$\sigma=0$.

19. A support according to claim 18, characterised in that the substrate (1) and the layer (2) are dielectric or little absorbent, the modules of the imaginary portion of their complex index being smaller than 0.01, the general conditions being reduced to the conditions:

$$n_1 e_1 \cos\theta_1 = \frac{\lambda}{4} + k\frac{\lambda}{2}$$

and $$n_1^2 = \frac{n_2^2 + \sqrt{n_2^2 \cos^2\theta_0(n_2^2 - n_0^2 \sin^2\theta_0)}}{n_2^2 + n_0^2 \cos^2\theta_0}$$

with integer k and with an uncertainty of 2% on the values of $n_1$ and $e_1$.

20. A support according to claim 19, characterised in that $\theta_0$ is smaller than 5°, the general conditions being reduced to $$\frac{2}{n_1^2} = \frac{1}{n_0^2} + \frac{1}{n_2^2}$$

and $$n_1 e_1 \cos\theta_1 = \frac{\lambda}{4} + k\frac{\lambda}{2}$$

with integer k and with an uncertainty of 2% on the values of $n_1$ and $e_1$.

21. An accessory configured for observing a liquid sample, said apparatus being formed of a Petri dish and of a support configured to receive said sample, wherein:
the support complies with claim 18,
the support is a bottom of the Petri dish.

22. A device for observing a sample including an optical microscope, a support intended for receiving said sample and two crossed polarisers, wherein in that the support complies with claim 18.

23. An accessory configured for observing a liquid sample, said apparatus being formed of a Perri dish and of a support configured to receive said sample, wherein:
the support complies with claim 17,
the support is a bottom of the Petri dish.

24. A device for observing a sample including an optical microscope, a support intended for receiving said sample and two crossed polarisers, wherein the support complies with claim 17.

25. A support intended for optimising the useful extinction coefficient of a polarising microscope for observing an object placed on the support or above the support in a medium (3) of refraction index $n_0$ with incident convergent spatially incoherent illumination under an angle $\theta_0$ at a wavelength $\lambda$, including
a substrate (1) of complex refraction index $n_2$,
a layer (2) of complex refraction index $n_1$ and of thickness $e_1$ on said substrate, said substrate and said layer being in a medium of index $n_0$ and being configured for observation with spatially incident convergent non-coherent illumination under an angle $\theta_0$ at a wavelength $\lambda$, said angle $\theta_0$ being with respect to and axis normal to an observation surface of the support
characterised in that,
the value of the thickness $e_1$ of the layer (2) is within 2% so that:

$$\frac{d}{de_1}\left(\frac{|\sigma|^2}{R_{NP}}\right) = 0$$

with $$R_{NP} = \frac{1}{4}|r_p + r_s|^2 + \frac{1}{4}|r_p - r_s|^2$$

and $$r_p = \frac{r_{01(p)} + r_{12(p)}e^{(-2j\beta_1)}}{1 + r_{01(p)}r_{12(p)}e^{(-2j\beta_1)}} \text{ and } r_s = \frac{r_{01(s)} + r_{12(s)}e^{(-2j\beta_1)}}{1 + r_{01(s)}r_{12(s)}e^{(-2j\beta_1)}}$$

and $$\sigma = \frac{\sigma_{01} + \sigma_{12}(1+\pi_{01})e^{(-2j\beta_1)} + \sigma_{01}\pi_{12}e^{(-4j\beta_1)}}{(1+r_{01(p)}r_{12(p)}e^{(-2j\beta_1)})(1+r_{01(s)}r_{12(s)}e^{(-2j\beta_1)})}$$

a formula wherein and $\sigma_{ik}$ and $\pi_{ik}$ represent respectively the sum and the product of the Fresnel coefficients of the different interfaces [(i,k)=(0,1) or (1,2)]

$$r_{ik(p)} = \frac{n_k\cos\theta_i - n_i\cos\theta_j}{n_k\cos\theta_i + n_i\cos\theta_k}$$

and $$r_{ik(s)} = \frac{n_i\cos\theta_i - n_k\cos\theta_k}{n_i\cos\theta_i + n_k\cos\theta_k}$$

and wherein $\beta_1 = \frac{2\pi n_1 e_1 \cos\theta_1}{\lambda}$, with $\cos\theta_1 = \sqrt{1 - (n_0/n_1)^2 \sin^2\theta_0}$.

26. A support according to claim 25, characterised in that the values of the refraction index $n_1$ and of the thickness $e_1$ of the layer (2) are within 2% such that:

$\sigma=0$.

27. An accessory configured for observing a liquid sample, said apparatus being formed of a Petri dish and of a support configured to receive said sample, wherein:

the support complies with claim 25, the support is a bottom of the Petri dish.

28. A device for observing a sample including an optical microscope, a support intended for receiving said sample and two crossed polarisers, wherein the support complies with claim 25.

* * * * *

UNITED STATES PATENT AND TRADEMARK OFFICE
CERTIFICATE OF CORRECTION

PATENT NO. : 7,652,762 B2 Page 1 of 1
APPLICATION NO. : 10/518075
DATED : January 26, 2010
INVENTOR(S) : Ausserre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1026 days.

Signed and Sealed this

Twenty-eighth Day of December, 2010

David J. Kappos
*Director of the United States Patent and Trademark Office*